United States Patent
Yoshida et al.

(10) Patent No.: US 7,572,927 B2
(45) Date of Patent: Aug. 11, 2009

(54) METHOD OF PRODUCING AN O-DISUBSTITUTED AROMATIC COMPOUND, AND METHOD OF PRODUCING A MONOSUBSTITUTED-MONOHALOAROMATIC COMPOUND

(75) Inventors: Jun-ichi Yoshida, Kyoto (JP); Aiichiro Nagaki, Kyoto (JP); Toshiki Nokami, Kyoto (JP)

(73) Assignee: Fujifilm Corporation, Minato-Ku, Tokyo (JP)

( * ) Notice: Subject to any disclaimer, the term of this patent is extended or adjusted under 35 U.S.C. 154(b) by 0 days.

(21) Appl. No.: 11/716,686

(22) Filed: Mar. 12, 2007

(65) Prior Publication Data

US 2008/0194816 A1 Aug. 14, 2008

(51) Int. Cl.
*C07F 7/00* (2006.01)
*C07F 7/04* (2006.01)
*C07C 27/00* (2006.01)

(52) U.S. Cl. .......... 556/95; 556/478; 568/878; 568/893

(58) Field of Classification Search .......... 556/95, 556/478; 568/878, 893
See application file for complete search history.

(56) References Cited

FOREIGN PATENT DOCUMENTS

JP 2006-241065 A 9/2006

OTHER PUBLICATIONS

"The 86th Annual Convention (Spring Session) of the Chemical Society of Japan, Preprints", Cover page, Contents, 3H2-45, and Colophon, published on Mar. 13, 2006.

J. Organometal. Chem., 1980, 193, 283-292.
"The 5th International Workshop on Micro Chemical Plants, Jan. 29-30, 2007, Kyoto Univeristy Katsura Campus, Kyota, Japan", cover p. 33, and Colophon.
IKCOC-10 Program and Abstracs, Nov. 13-17, 2006, Rihga Royal Hotel Kyoto, Japan, Cover page, p. 218 and Colophon.
J. Am Chem. Soc., Published on Web Feb. 27, 2007.
J. Org. Chem., 1984, 49, 2792-2795.
Henry Gilman et al., "Some Reactions of o-Halobromobenzenes with n-Butyllithium", J. Amer. Chem. Soc., May 20, 1956, pp. 2217-2222.
Frédéric Leroux et al., "The "Aryne" route to Biaryls Featuring Uncommon Substituent Patterns", Angew. Chem. Int. Ed., 2002, pp. 4272-4274, vol. 41-No. 22, Wiley-VCH Verlag GmbH & Co., KGaA, Weinheim, Germany.
Laure Boymond et al., "Preparation of Highly Functionalized Grignard Reagents by an Iodine-Magnesium Exchange Reaction and its Application in Solid-Phase Synthesis", Angew. Chem. Int. Ed, 1998, pp. 1701-1703, vol. 37-No. 12, Wiley-VCH Verlag GmbH, D69451 Weinheim, Germany.

(Continued)

*Primary Examiner*—Porfirio Nazario Gonzalez
(74) *Attorney, Agent, or Firm*—Buchanan Ingersoll & Rooney PC

(57) ABSTRACT

A method of producing an o-disubstituted aromatic compound, containing: continuously conducting at least the following steps (a) to (d):
(a) a step of mono-lithiating one halogen atom of an o-dihaloaromatic compound, using a first microreactor;
(b) a step of making the thus-obtained monolithiated product to react with an electrophilic compound, using a second microreactor, to obtain a monosubstituted-monohaloaromatic compound;
(c) a step of lithiating the other halogen atom of the o-dihaloaromatic compound, using a third microreactor; and
(d) a step of making the thus-obtained lithiated product successively to react with an electrophilic compound, using a forth microreactor.

6 Claims, 2 Drawing Sheets

OTHER PUBLICATIONS

Chemfiles-Enabling Technologies, Microreactor Technology, 2005, pp. 1-20, vol. 5-No. 7, Aldrich Advancing Science, Milwaukee, Wisconsin, USA.

O. Hirotsugu Usutani et al. "Selective Monolithiation of Dihaloarenes using Microreactor", The 86th Annual Convention (Spring Session) of the Chemical Society of Japan, Cover page, Contents, 3H2-45 to 3H2-48, pp. 374 and 996, vol. 59-No. 3, Mar. 13, 2006, Department of Synethetic Chemistry and Biological Chemistry, Graduate School of Engineering, Kyoto University, Japan and English-Language translation.

Yutaka Tomida, "Lithiation of Polyhaloarenes using Microreactors", presented Jun. 24, 2006 in the Inventor's Yoshida's Laboratory, Department of Synethetic Chemistry and Biological Chemistry, Graduate School of Engineering, Kyoto University, Japan.

Yousuke Ushiogi et al., "Synthesis of Photochromic Diarylethenes using a Microflow System", The 9th International Conference on Microreaction Technology, Berlin, Germany, Sep. 6-8, 2006, Cover page, Contents of Preprints of the Conference, Dechema, Frankfurt, Germany.

Aiichiro Nagaki et al., "Integrated Micro Flow synthesis Based on Sequential Br-Li Exchange Reactions of p-, m-, and o-Dibromobenzenes", Chemistry Asian Journal, 2007, pp. 1513-1523, vol. 2, Wiley-VCH Verlag GmbH & Co. KgaA, Weinheim, Germany.

METHOD OF PRODUCING AN O-DISUBSTITUTED AROMATIC COMPOUND, AND METHOD OF PRODUCING A MONOSUBSTITUTED-MONOHALOAROMATIC COMPOUND

FIELD OF THE INVENTION

The present invention relates to a method of producing a target o-disubstituted aromatic compound efficiently with a high yield, and a high selectivity, in which a variety of substituents are introduced, using an o-dihaloaromatic compound as a raw material. Further, the present invention relates to a method of producing a target monosubstituted-monohaloaromatic compound, with a high selectivity, in which a variety of substituents are introduced, using an o-dihaloaromatic compound as a raw material.

BACKGROUND OF THE INVENTION

An o-bromophenyl lithium can be synthesized by reacting ortho-dibromobenzene in a specific mixed solvent at −110° C. via a metal-halogen exchange reaction. However, it is known that the thus-lithiated o-bromophenyl lithium is so unstable that if a temperature is elevated to −90° C., the lithiated compound is easily decomposed to form benzyne which resultantly forms a series of by-products (Chen, L. S.; Chen, G. J.; Tamborski, C. J. Organometal. Chem., 1980, 193, 283-292). Therefore, it has been thought that from the necessity of severe temperature control to −90° C. or lower, it is difficult to cause reaction of the above-described lithiated compound with an electrophilic compound at a higher temperature than −90° C.

In this aspect, the present inventors proposed a method for obtaining a bromobenzene, at −78° C., by using a microreactor, to obtain a mono-lithiated product of 1,2-dibromobenzene, and then reacting the mono-lithiated product with methanol, to cause protonation (Hirotsugu Usutani, Toshiki Nokami, Hideho Okamoto, Jun-ichi Yoshida, the 86th Annual Convention (Spring Session) of Nippon Kagaku Kai (the Chemical Society of Japan), Preprints, 3H2-45 (2006), published on Mar. 13, 2006; the disclosure of which is herein incorporated by reference).

Further, the present inventors proposed a method in which a halogen compound is allowed to react with a lithium agent using a microreactor to obtain a mono-lithiated product of the halogen compound, and then the thus-obtained mono-lithiated product is allowed to react with an electrophilic compound (JP-A-2006-241065 ("JP-A" means unexamined published Japanese patent application)). However, this publication discloses a reaction of only one halogen atom of the halogen compound, but the publication is silent on that an o-dihaloaromatic compound having two halogen atoms adjacent to each other on the aromatic ring be converted to the corresponding o-disubstituted aromatic compound. Besides, the method described in this patent publication is characterized in that mono-lithiation can be performed at the reaction temperature of from −10 to 40° C. that is extremely higher than a conventional temperature, but there is no description that an o-dihaloaromatic compound having two halogen atoms adjacent to each other on the aromatic ring be converted to the corresponding o-disubstituted aromatic compound.

Accordingly, it has been eagerly desired the development of a method capable of producing an o-disubstituted aromatic compound, efficiently with a high yield, by electrophilic substitution reaction of each of two halogen atoms of an o-dihaloaromatic compound.

SUMMARY OF THE INVENTION

The present invention resides in a method of producing an o-disubstituted aromatic compound, which comprises, continuously conducting at least the following steps:
(a) a step of mono-lithiating one halogen atom of an o-dihaloaromatic compound, using a first microreactor;
(b) a step of making the thus-obtained monolithiated product to react with an electrophilic compound, using a second microreactor, to obtain a monosubstituted-monohaloaromatic compound;
(c) a step of lithiating the other halogen atom of the o-dihaloaromatic compound, using a third microreactor; and
(d) a step of making the thus-obtained lithiated product successively to react with an electrophilic compound, using a forth microreactor.

Other and further features and advantages of the invention will appear more fully from the following description, appropriately referring to the accompanying drawings.

DETAILED DESCRIPTION OF THE INVENTION

Figure 1:
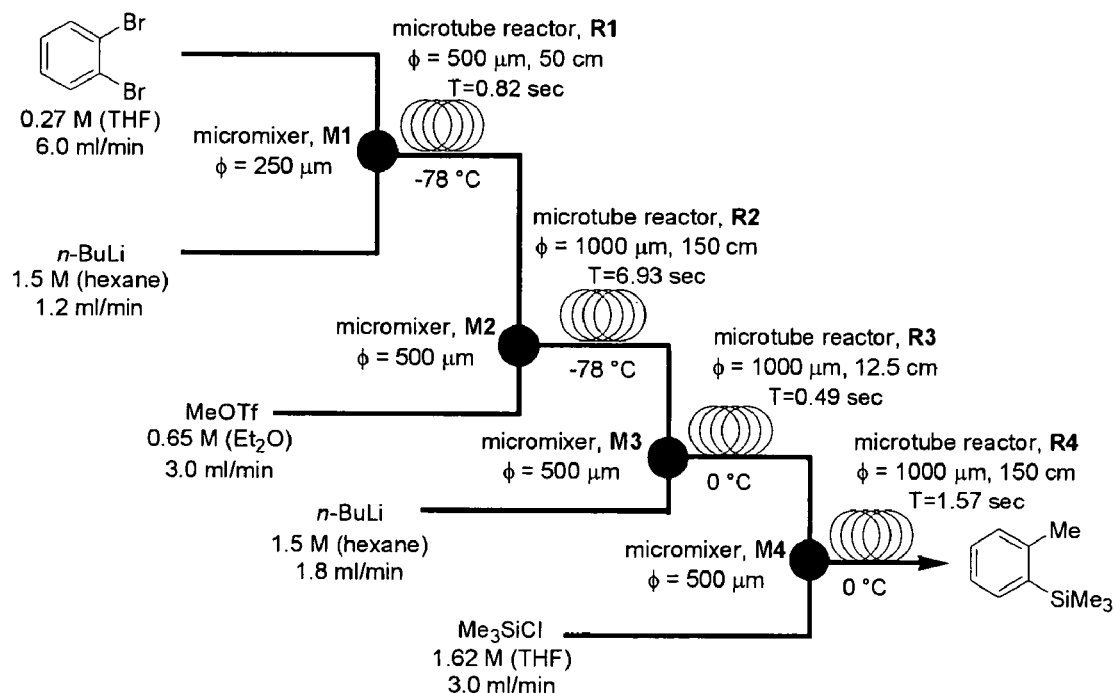
FIG. 1 is an explanatory view that shows a symbolic view of the microreactor apparatuses used in Example 1, accompanied with reaction conditions.

The present inventors have intensively studied, in order to develop a method of synthesizing o-disubstituted aromatic compounds, as exemplified by o-disubstituted benzenes, while preventing benzyne that is a by-product in the above from being formed. As a result of the studies, we found the followings: That by conducting a lithiation reaction of a halogenated benzene compound using a microreactor, and making the thus-obtained lithiated product react with an electrophilic compound (an electrophile), it is possible to perform the reaction at −78° C. that is remarkably higher than −110° C. as described in the above non-patent literature; That, in particular, a by-product of the above-described benzyne is considerably minimized in the reaction product, consequently in succession, the remaining halogen atom at the ortho position of the monosubstituted-monohalo benzene compound can be lithiated in a microreactor, under the condition of about 0° C.; That the thus-obtained lithiated product is subjected to an electrophilic substitution reaction with an electrophilic compound, thereby to introduce two substituents adjacent to each other; Consequently, that o-disubstituted benzenes can be obtained efficiently with a high yield and a high selectivity. The present invention has been attained basis on the those findings.

According to the present invention, there is provided the following means:
(1) A method of producing an o-disubstituted aromatic compound, comprising: continuously conducting at least the following steps:

(a) a step of mono-lithiating one halogen atom of an o-dihaloaromatic compound, using a first microreactor (first step);
(b) a step of making the thus-obtained monolithiated product to react with an electrophilic compound, using a second microreactor, to obtain a monosubstituted-monohaloaromatic compound (second step);
(c) a step of lithiating the other halogen atom of the o-dihaloaromatic compound, using a third microreactor (third step); and
(d) a step of making the thus-obtained lithiated product successively to react with an electrophilic compound, using a forth microreactor (fourth step);

(2) The method of producing an o-disubstituted aromatic compound described in (1), wherein a reaction temperature in a flow channel of each of the first microreactor and the second microreactor is in the range of from −85° C. to −60° C.;

(3) The method of producing an o-disubstituted aromatic compound described in (1), wherein the electrophilic compound to be used is an aldehyde compound, a ketone compound, a chlorosilane compound, a chlorostannane compound, a halogenated alkyl compound, a sulfonic acid ester compound, or a boric acid ester compound;

(4) The method of producing an o-disubstituted aromatic compound described in (1), wherein the minimum length of a flow channel cross-section of the first microreactor is in the range of from 10 μm to 500 μm, and the minimum length of a flow channel cross-section of each of the second to fourth microreactors is independently in the range of from 10 μm to 2,000 μm;

(5) A method of selectively producing a monosubstituted-monohaloaromatic compound, comprising: continuously conducting at least the following steps:
(a) a step of mono-lithiating one halogen atom of an o-dihaloaromatic compound, using a first microreactor (first step);
(b) a step of making the thus-obtained monolithiated product to react with an electrophilic compound, using a second microreactor, to obtain a monosubstituted-monohaloaromatic compound (second step);

(6) The method of producing an o-disubstituted aromatic compound described in (5), wherein a reaction temperature in a flow channel of each of the first microreactor and the second microreactor is in the range of from −85° C. to −60° C.;

(7) The method of producing an o-disubstituted aromatic compound described in (5), wherein the electrophilic compound to be used is an aldehyde compound, a ketone compound, a chlorosilane compound, a chlorostannane compound, a halogenated alkyl compound, a sulfonic acid ester compound, or a boric acid ester compound; and (8) The method of producing an o-disubstituted aromatic compound described in (5), wherein the minimum length of a flow channel cross-section of the first microreactor is in the range of from 10 μm to 800 μm, and the minimum length of a flow channel cross-section of the second microreactor is independently in the range of from 10 μm to 5,000 μm.

In the present invention, the term "successively conducting the steps of (a) to (d)" as referred to herein means that a reaction of each step is successively conducted in flow, and consequently it is not to be meant to exclude to optionally introduce, for example, a purification treatment, between each of the two steps.

The method of the present invention is directed to a method of producing an o-disubstituted aromatic compound from an o-dihaloaromatic compound, using a microreactor.

The o-dihaloaromatic compound that can be used in the present invention can be represented by formula (I) set forth below.

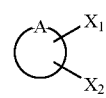

Formula (I)

In formula (I), a ring represented by A represents an aromatic ring or a heteroaromatic ring. $X_1$ and $X_2$ each represent a halogen atom, which are located adjacent to each other on the above-described ring, and may be the same or different from each other.

In the present invention, in the first step and the second step, the halogen atom $X_1$ one of the two is substituted with an electrophilic group after lithiation; and, in the third step and the fourth step, the halogen atom $X_2$ adjacent to the halogen atom $X_1$ is substituted with an electrophilic group after lithiation, thereby to obtain an o-disubstituted aromatic compound, as can be represented by formula (II) set forth below.

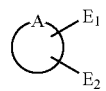

Formula (II)

In formula (II), $E_1$ and $E_2$ each represent an electrophilic group by which the above-described $X_1$ and $X_2$ adjacent to each other are replaced, and $E_1$ and $E_2$ may be the same or different from each other. A has the same meaning as described above.

The following is an explanation of the microreactor for use in the present invention.

The microreactor (micro flow reactor) for use in the present invention is a micro flow reactor that is composed of a mixing section (a micro mixer) for mixing a plurality of liquids and a reactor section subsequent therefrom. The minimum length of the channel cross-section of the mixing section and the reactor section is typically in the range of from several μm to several thousands μm. The minimum length of the channel cross-section and other length can be suitably selected depending on the purposes.

The cross-sectional shape of the channel of the microreactor is not limited in particular, but may be suitably selected depending on the purposes. Examples of the shape include a circle, a rectangle, a half circle, and a triangle. The liquid may be caused to flow through a plurality of separated channels inside.

There is no particular limitation in the length in the direction of a flow as well as the shape of a reactor section of the microreactor, and they may be suitably selected depending on the conditions such as the kind of reaction and the reaction time.

A reaction temperature can be controlled according to the method exemplified below: A method, in which the whole or a part of the microreactor is placed in a thermostat; a method in which a heat medium (refrigerant) is caused to flow through another channel provided near the channel; and a method in which a cooler or a heater is provided near the channel.

Multi stage reactions may be conducted, according to a method in which a plurality of the microreactors are connected together for use, and a method in which an apparatus incorporated therein a plurality of the microreactors is used.

The microreactor is defined as an apparatus that has micro channels having a very small equivalent diameter of generally several mm or less, and preferably less than 500 nm, and that a reaction is conducted in the micro channels. In other words, the microreactor is a reactor for conducting a reaction under a stationary state, using a miniaturized flow reactor or a static micro mixer. Herein, the term "equivalent diameter" means a diameter of a circle into which the channel cross-section is converted. The static micro mixer is an apparatus represented by a mixer having a microscopic channel for mixing, as described in, for example, WO 96/30113, or a mixer as described by W. Ehrfeld, V. Hessel, and H. Lowe in "Microreactors", the Chapter 3, published by Wiley-VCH.

In the technical field of the microreactor in which the measure of a micro channel is a micro scale, each of a size and a flow velocity is small and a Reynolds number is 200 or less, and a flow of the liquid is dominant in a laminar flow. A plurality of fluids to react flow to react each other, while flowing each in a laminar flow state inside the channel and causing diffusion of the molecules in the fluids by a spontaneous behavior thereof. In the microreactor, a reaction time is easily controlled by a residence time inside the microreactor because a reaction is performed by a flow. In addition, owing to a large specific surface (a surface area of the fluid involved in a reaction per unit volume), a heat balance can be efficiently controlled. Thus, a temperature at the time of reaction can be precisely and efficiently controlled. Consequently, the selectivity of a reaction, especially a rapid reaction, can be remarkably improved. Furthermore, since a heat exchange (heat transfer) time (t) is in proportion to $d^2/\alpha$ (d is a width of a micro channel; $\alpha$ is a thermal diffusivity of liquid) according to the diffusion theory, the heat exchange efficiency is further improved as a micro channel width becomes smaller.

As the microreactor for use in the present invention, use can be made of known apparatuses, commercially available products, and products newly designed for a reaction in interest as a prototype. As the microreactor on the market, there can be exemplified a microreactor provided with an inter digital channel structure, a single mixer and a caterpillar mixer made by Institut für Mikrotechnik Mainz (IMM); a micro glass reactor made by Micro Glass Corporation; CYTOS made by CPC Systems; YM-1 and YM-2 model mixers made by Yamatake Corporation; a mixing tee and a tee (T-letter connector) made by Shimadzu GLC Corporation; an IMT chip reactor made by Institute of Micro Chemistry; and a micro high mixer developed by Toray Engineering, each of which can be used in the present invention.

The minimum constitution units of the microreactor for use in the present invention are a micro mixer and a tube reactor. Further, a microreactor for a multistage reaction can be also composed by connecting a plurality of micro mixers and tube reactors. It is necessary for a synthetic reaction to compose a flow reactor incorporated a microreactor therein. The reactor configuration in that case is composed of, for example, a micro mixer, a tube reactor, a feed pump for supplying raw chemicals to the microreactor, a thermostat and a circulator, a heat exchanger for a temperature controlling, a temperature, sensor, a flow sensor, a pressure sensor for measuring pressure inside the piping, and a product tank for storing a product solution.

The micro mixer for use in the present invention preferably has a micro channel for mutually mixing fluids or compounds in a solution or liquid state. Further, even in the use of a simple tee of T-model channel for mixing two sub-streams, a satisfactory mixing and reaction performance is attained by the use of a contracted or merged flow effect or turbulence of flow owing to a high stream velocity. Inside the micro mixer, a reaction is initiated by mixing, and at the same time exothermic heat generates by the reaction. By the Kenic model static mixer of conventional size in which a channel sectional area is large, a satisfactory mixing performance cannot be obtained in a mixing reaction due to a wide channel size. In addition, the static mixer of conventional size is not satisfactory in the capacity for eliminating exothermic heat generated at the time of reaction. Based on these points, the static mixer of conventional size is distinguished from the micro mixer for use in the present invention. In the case where a reaction is conducted by mixing two sub-streams, a cross-sectional area of the sub-stream ordinarily is determined, based on a channel sectional area of the mixer used in the reaction. The channel of the micro mixer for use in the present invention has a cross-sectional area of generally from 100 $\mu m^2$ to 16 $mm^2$, preferably from 1,000 $\mu m^2$ to 4.0 $mm^2$, more preferably from 10,000 $\mu m^2$ to 2.1 $mm^2$, and especially preferably from 190,000 $\mu m^2$ to 1 $mm^2$. The cross-sectional shape of the channel is not limited in particular, but may be a circle, a rectangle, a half circle, or a triangle.

A tube that is connected to the rear of a micro mixer has functions of both diffusion mixing and mixed reaction of raw materials, and elimination of heat of reaction. As the inner diameter of the tube becomes smaller, a diffusion length becomes shorter and the reaction rate increases. Therefore, the tube having a smaller inner diameter is more advantageous to the shortage of reaction time. Besides, as the inner diameter of the tube becomes smaller, a heat exchange capacity increases. Accordingly, the tube having a smaller inner diameter is also useful for a reaction accompanied with a large exothermic heat. However, as the inner diameter of the tube becomes smaller, a pressure loss at the time of flowing a liquid increases. Therefore, the pump to be used must be a special pressure-resistant one for high pressure. Besides, a flow rate of the running liquid is limited, and consequently a structure of the micro mixer is also restricted, which causes inexpediences. The inner diameter of the tube for use in the present invention has an equivalent diameter generally in the range of from 100 µm to 4 mm, preferably from 250 µm to 3 mm, more preferably from 300 µm to 2 mm, and especially preferably from 500 µm to 1 mm.

The material of the microreactor is not limited in particular, but may be properly selected in accordance with a necessary property such as heat resistance, pressure resistance, solvent resistance, and ease of processing. For example, there can be preferably used any of metals, such as stainless steel, titanium, cupper, nickel, and aluminum; glass, foturane glass, various kinds of ceramics, PEEK resins, plastics, silicon; and Teflon (trade name, tetrafluoroethylene) resins, such as PFA and TFAA.

The method of producing the microreactor is not limited in particular, but may be properly selected in accordance with purposes. For example, the microreactor may be produced by a fine processing technique. The followings are fine processing techniques that are suitable for the production of the microreactor:

(a) LIGA technique that is a combination of X ray lithography and electroplating
(b) High aspect ratio photolithography using EPON SU8
(c) Mechanical micro cutting (for example, a micro drill processing with a rapid rotation of a drill having a drill diameter of a micro order)

(d) High aspect ratio processing method of silicon according to Deep RIE
(e) Hot Emboss processing method
(f) Photo-shaping method
(g) Laser processing method
(h) Ion beam method Any of the above-described fine processing techniques may be applied to the microreactor for use in the present invention, without any particular limitation.

A flow rate of the fluid to be fed to the microreactor (a speed of the liquid to be fed) is properly selected in accordance with various conditions such as kinds of reaction, a size or shape and length of the channel, and a temperature. For example, in the case of using a mixing tee having an inner diameter $\phi$ of 0.8 mm and a tube having an inner diameter $\phi$ of 0.8 mm, the flow rate is generally in the range of from 0.1 μl/min to 1000 μl/min, preferably from 0.1 ml/min to 100 ml/min, more preferably from 1 ml/min to 50 ml/min, and especially preferably from 5 ml/min to 30 ml/min. A flow velocity of each of raw materials to be fed to the microreactor may be the same or different from each other. As a pump for feeding a liquid, there can be used any of feeding pumps for industrial use. Of these pumps, preferred are machines of the type that generate the least possible pulsating (pulsating motion) at the time of feeding a liquid. Preferable examples of the pump include a plunger pump, a gear pump, a rotary pump, and a diaphragm pump.

In the microreactor, liquids or solution-form compounds are mixed by a kinetic energy of both a flow fluid and a solution, thereby reacting with each other. If necessary, there may be added energy for accelerating the mixing, such as vibration energy, from outside of the microreactor. With respect to the mixing, there can be changed from a static mixing (laminar flow) to a dynamic mixing (turbulent flow), in accordance with a flow velocity or a flow velocity and a shape of the reactor (for example, shapes such as a three dimensional shape of the fluid-interfacing portion and a shape of a flexing portion of the channel, coarseness of the channel). Any one of the laminar flow and the turbulent flow may be used for mixing.

The reaction that is involved in the present invention is illustrated by the following scheme:

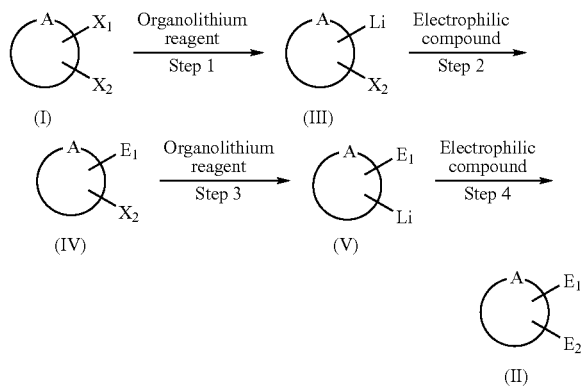

In the above scheme, A, $X_1$, $X_2$, $E_1$ and $E_2$ have the same meanings as described above, respectively. Li on the ring represents Li substituted in place of $X_1$ or $X_2$ upon the lithiation.

In the step 1 according to the present invention, a temperature at which a lithiated product is formed by a lithiation reaction of $X_1$ in the first microreactor is preferably in the range of from −85° C. to −60° C., more preferably from −80° C. to −60° C., and especially preferably from −80° C. to −65° C. If the temperature is too low, it takes a long time for a reaction to perform mono-lithiation of one halogen group. On the other hand, if the temperature is too high, it is difficult to prevent the lithiated product from decomposition to benzyne after the mono-lithiation reaction of the halogen group. Besides, in the step 3, a temperature at which a lithiated product is formed by a lithiation reaction of $X_2$ in the third microreactor is preferably in the range of from −78° C. to −26° C., and more preferably from −24° C. to 0° C. If this reaction temperature is too low, it necessarily takes a long time for a reaction to perform mono-lithiation of the other halogen group. On the other hand, if the temperature is too high, it is difficult to prevent decomposition of the lithiated product in the halogen group.

The reaction time in each step in the present invention is defined by a residence time from starting of mixing of raw liquids in a micro mixer until the resulting reaction product is discharged to the outside of the system from an outlet through a tube connected to a rear portion of the micro mixer. On the other hand, the reaction time in the present invention is defined by a sum of the residence time from starting of mixing of raw liquids in a micro mixer of the first step, via the steps 2 and 3, followed by starting of mixing with an electrophilic compound in a micro mixer of the step 4, until the resultant reaction product is discharged to the outside of the system from an outlet through a tube connected to a rear portion of the micro mixer. In the present invention, it is also possible to control a reaction time by altering a flow rate of the raw material to be fed. However, it is preferable to set a reaction time by a method of altering a length and an equivalent diameter of the tube so that a suitable residence time can be obtained, in accordance with a flow rate of the raw material solution to be fed to the microreactor, because it is often that the flow rate range suitable for mixing has been previously set in the microreactor. The residence time inside the microreactor varies, depending on parameters such as reactivity of a halogen compound and an organolithium reagent, a concentration of the reagent(s), a reaction temperature, and stability of the lithium compound.

A halogen-lithium exchange reaction is an extremely rapid reaction. Moreover, the thus-formed lithium intermediate is low in thermal stability. Consequently, for a reaction time of lithiation inside the channel of the first and the third microreactors, it is enough to set to preferably 0.10 sec or more, and more preferably 0.40 sec or more. If the reaction time is too short, the reaction does not satisfactorily progress as a natural consequence. On the contrary, even though the reaction time is long, a problem arises that it is difficult to prevent the lithiated product from decomposition. Therefore, the reaction time is generally set within 1.65 sec.

An amount to be used of the organolithium reagent in the first step or the third step varies, depending on the kind of an o-dihaloaromatic compound to be used, but it is preferably in the range of from 0.1 mol to 2.0 mol, more preferably from 0.5 mol to 1.3 mol, and furthermore preferably from 0.9 mol to 1.1 mol, per mol of the substrate (o-dihaloaromatic compound or monosubstituted-monohaloaromatic compound).

In the step 2 of the present invention, a reaction temperature for the electrophilic substitution reaction of the lithiated product in the second microreactor is preferably in the range of from −85° C. to −60° C., more preferably from −80° C. to −60° C., and especially preferably from −80° C. to −65° C. If the reaction temperature is too low, it takes a long time to conduct a reaction of the lithiated product with an electrophilic reagent. On the other hand, if the reaction temperature is too high, it is difficult to terminate the above-described reaction before occurrence of decomposition of the lithiated product to benzyne. Besides, a reaction temperature for the electrophilic substitution reaction of the lithiated product in the step 4 is preferably in the range of from −78° C. to −26° C., and more preferably from −24° C. to 0° C. If the reaction temperature is too low, it takes a long time to conduct a reaction of the lithiated product with an electrophilic reagent. On the other hand, if the reaction temperature is too high, it is difficult to terminate the above-described reaction of the lithiated product with an electrophilic compound before occurrence of decomposition thereof.

For a reaction time of the electrophilic substitution reaction in microreactors in the steps 2 and 4, it is enough to be preferably 0.06 sec or more, and more preferably 1.15 sec or more. If the reaction time is too short, the reaction does not satisfactorily progress as a natural consequence. On the contrary, even though the reaction time is long, it is difficult to prevent a side reaction from the product from causing. Therefore, the reaction time is generally set within 9.25 sec.

An amount to be used of the electrophilic compound is preferably in the range of from 0.1 mol to 2.0 mol, more preferably from 0.5 mol to 1.3 mol, and furthermore preferably from 0.9 mol to 1.1 mol, per mol of the lithiated aromatic compound.

In the present invention, if a reaction is performed in a channel of the microreactor, a micro channel works as a micro reaction field, at which a high speed and efficient diffusion and mixing take place. Consequently, a target o-disubstituted aromatic compound can be produced with a high yield and a high selectivity according to the present invention. A minimum section length of the channel of the microreactor is preferably in the range of from 10 μm to 800 μm, and more preferably from 10 μm to 500 μm in the first microreactor; and, in the second to fourth microreactors, the minimum section length each independently is preferably in the range of from 10 μm to 5,000 μm, and more preferably from 10 μm to 2,000 μm.

In so far as a reaction condition applied to the step 4 in the present invention is the condition under which a lithiated product does not decompose, there may be used a batch reaction that is conducted by feeding of the thus-formed lithiated product to a vessel such as a flask and a reaction tank, followed by addition of an electrophilic compound thereto for reaction. However, preferred is a continuous reaction using a microreactor.

In the present invention, it is preferable to shorten the minimum section length of the channel of the microreactor to be used in the step 1 than that of the microreactor in each of the steps 1 to 4.

In the microreactors in the steps 2 to 4, it is preferable to minimize a size of the minimum section length of the channel within such a range that no problem arises by increase of pressure loss.

A channel length of the microreactor is preferably in the range of from 30 mm to 1,000 mm in a lithiation reaction of the steps 1 and 3, respectively; and the channel length in the case of electrophilic substitution reaction in the steps 2 and 4 is preferably in the range of from 30 mm to 2,000 mm, and more preferably from 500 mm to 2,000 mm, respectively.

A reaction time (residence time) of a reaction solution in the above-described microreactor can be attained by controlling the channel length and the flow rate.

In the present invention, the product may be taken out from the reaction system at the time the completion up to the step 2, and the thus-taken-out product can be used as it is. The thus-taken-out compound at the time of completion of the step 2, is the monosubstituted-monohaloaromatic compound represented by formula (IV). The thus-obtained monosubstituted-monohaloaromatic compound is a useful compound, for example, as a synthetic intermediate. As described in the above, one of the characteristics of the present invention is that a useful compound can be selectively and effectively obtained at the time when the above-described step 2 has been completed.

Preferable specific examples are shown below, with respect to the compound represented by formula (IV), which is obtained by the method of the present invention, and which can be taken out at the time of completion of the step 2, but the present invention should not be construed as being limited to those.

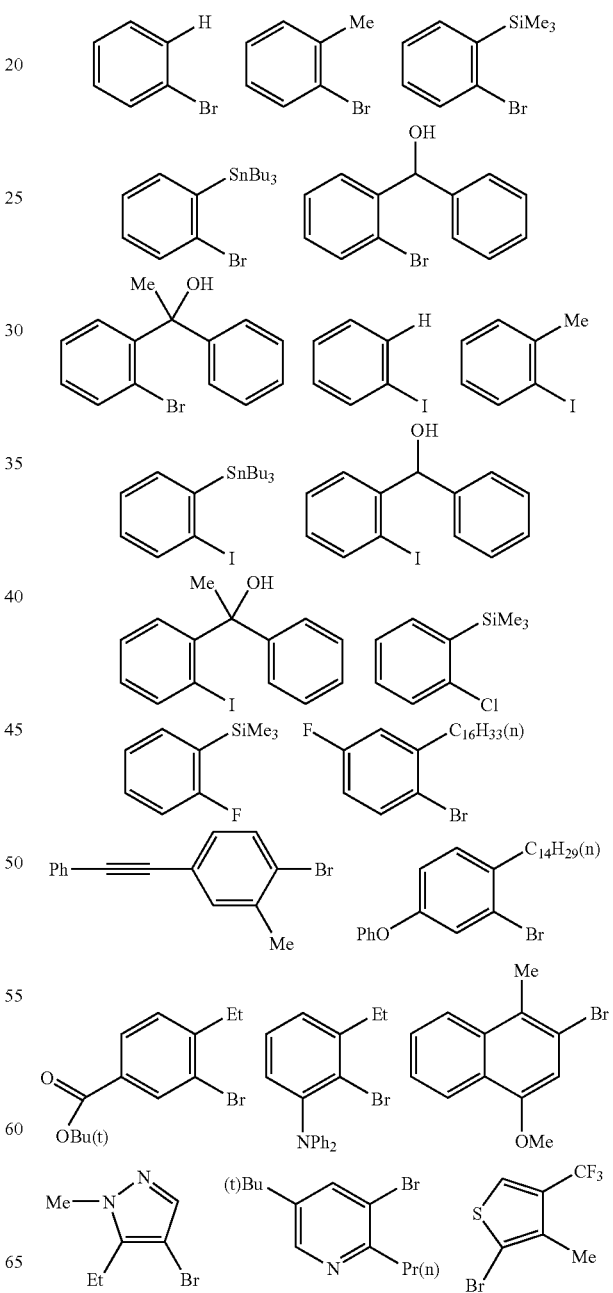

-continued

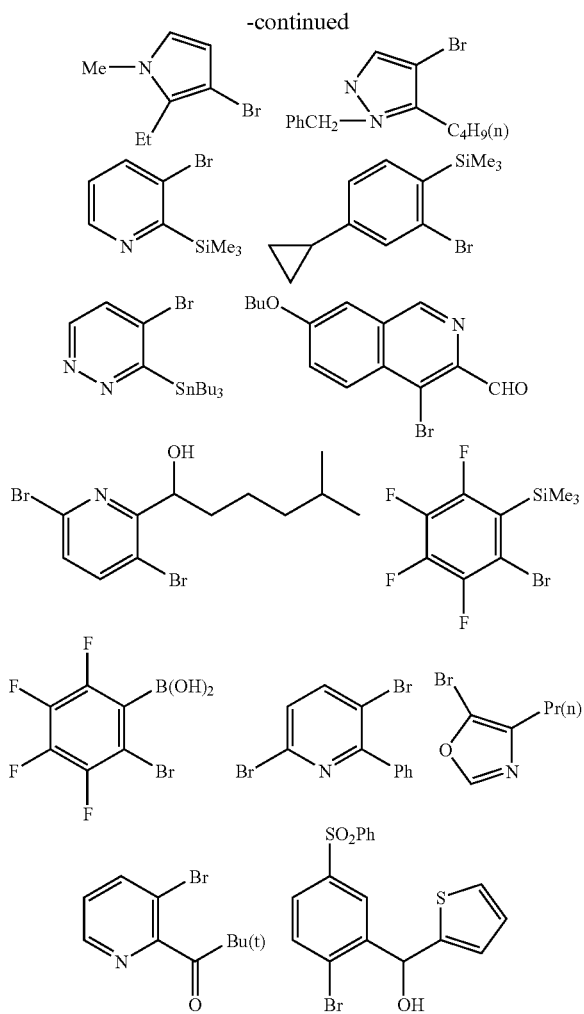

In the present invention, the progress of the reaction can be monitored, using any of various known analytical instrument. The product ratio can be confirmed by means such as high performance liquid chromatography and capillary gas chromatography. Further, the reaction can be monitored on-line, by monitoring the change of absorbance using such instrument as an on-line FT-IR spectrometer or an on-line NIR spectrometer.

The compounds that can be used in the present invention are explained below. Examples of a halogen atom substituting on the o-dihaloaromatic compound that can be used in the present invention include chlorine, bromine and iodine. Of these atoms, bromine and iodine are preferable from the viewpoint of high reactivity. Two halogen atoms may be the same or different from each other. Accordingly, the compound may be a chloro-bromo form, an iodo-bromo form, or a chloro-iodo form.

The compound represented by formula (I) according to the present invention is an o-dihaloaromatic compound. This means to include such aromatic heterocyclic compounds as illustrated above. The ring represented by A specifically represents a monocyclic or polycyclic 6- to 10-membered aromatic ring exemplified by benzene, naphthalene, anthracene and phenanthrene; and a monocyclic or polycyclic 5- to 10-membered aromatic heterocycle that contains 1 to 4 atoms selected from nitrogen, oxygen and sulfur, and that is exemplified by thiophene, furan, pyran, pyridine, pyrrole, pyrazine, azepine, azocine, azonine, azecine, oxazole, thiazole, pyrimidine, pyridazine, triazine, triazole, tetrazole, imidazole, pyrazole, morpholine, thio morpholine, piperidine, piperazine, quinoline, isoquinoline, indole, isoindole, quinoxaline, phthalazine, quinolizine, quinazoline, quinoxaline, naphthyridine, chromene, benzofuran, and benzothiophene. Of these aromatic rings, preferred are monocyclic or polycyclic aromatic rings with a more preferable ring being benzene.

Further, the ring represented by A may have a substituent. There is no particular limitation in the number of substituents and the kind of the substituent. Specific examples of the substituent include a straight, branched or cyclic alkyl group having 1 to 20 carbon atoms, including an alkyl group substituted with a cycloalkyl group, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, cyclopropyl, cyclobutyl, cyclopentyl, cyclohexyl, cycloheptyl, cyclooctyl, cyclononyl, and cyclodecyl groups; a straight, branched or cyclic alkenyl group having 2 to 20 carbon atoms, such as vinyl, allyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, hexadienyl, and dodecatrienyl groups; a straight, branched or cyclic alkynyl group having 2 to 20 carbon atoms, such as ethynyl, butynyl, pentynyl, hexynyl, heptynyl, octynyl, nonynyl, cyclooctynyl, cyclononynyl, and cyclodecynyl groups; a monocyclic or polycyclic 5- to 10-membered aryl group, such as phenyl, naphthyl, and anthranyl groups; an alkoxy group having 1 to 20 carbon atoms, such as methoxy, ethoxy, propoxy, butoxy, pentyloxy, hexyloxy, heptyloxy, octyloxy, nonyloxy, decyloxy, dodecyloxy, hexadecyloxy, and octadecyloxy groups; an aryloxy group, such as phenoxy and naphthyloxy groups; an alkylthio group having 1 to 20 carbon atoms, such as methylthio, ethylthio, propylthio, butylthio, pentylthio, hexylthio, heptylthio, octylthio, nonylthio, decylthio, dodecylthio, hexadecylthio, and octadecylthio groups; an arylthio group, such as phenylthio and naphtylthio groups; a substituted carbonyl group having 2 to 20 carbon atoms, such as acyl, benzoyl and naphthoyl groups, more specifically acetyl, propanoyl, butanoyl, pentanoyl, hexanoyl, and heptanoyl groups; a substituted oxycarbonyl group, such as methoxycabonyl, ethoxycabonyl, tert-butoxycarbonyl, n-decyloxycarbonyl, and phenoxycarbonyl groups; a substituted carbonyloxy group having 2 to 20 carbon atoms, such as acyloxy, benzoyloxy and naphthoyloxy groups, more specifically acetyloxy, propanoyloxy, butanoyloxy, pentanoyloxy, hexanoyloxy, and heptanoyloxy groups; a substituted sulfonyl group, such as methylsulfonyl, ethylsulfonyl, propylsulfonyl, butylsulfonyl, pentylsulfonyl, hexylsulfonyl, heptylsulfonyl, octylsulfonyl, phenylsulfonyl, and naphthylsulfonyl groups; a carbamoyl group substituted with one or two groups selected from an alkyl group, an alkenyl group and an aryl group, such as N-methylcarbamoyl, and N,N-diphenylcarbamoyl groups; a sulfamoyl group substituted with one or two groups selected from an alkyl group, an alkenyl group and an aryl group, such as N-phenylsulfamoyl, and N,N-diethylcarbamoyl groups; a substituted carbonylamino group having 2 to 20 carbon atoms, such as acylamino, benzoylamino, and naphtoylamino groups, more specifically acetylamino, tert-butylcarbonylamino, and n-hexylcarbonylamino groups; an ureido group substituted with one or two groups selected from an alkyl group, an alkenyl group and an aryl group, such as N-methylureido, and N,N-diethylureido groups; a substituted sulfonylamino group having 1 to 20 carbon atoms, such as sulfonylamino, phenylsulfonylamino and naphthylsulfonylamino groups, more specifically methylsulfonylamino, tert-butylsulfonylamino, and n-octylsulfonylamino groups; a mono- or di-substituted amino group, such as metylamino, phenylamino, tert-butoxycarbonylamino, pivaloylamino, benzylamino, phthaloylamino, N,N-dimethylamino, N,N-diethylamino, N,N-diphenylamino, and N-methyl-N-phenylamino groups; a nitro group; a cyano group; a substituted silyl group, such as trimethylsilyl, and triethylsilyl groups; a halogen atom, such as fluorine, bromine, chlorine and iodine; a group given by a monocyclic or polycyclic 5- to 10-membered hetero ring containing 1 to 4 atoms selected from nitrogen, oxygen and sulfur, such as thiophene, furan, pyran, pyridine, pyrrole, pyrazine, azepine, azocine, azonine, azecine, oxazole, thiazole, pyrimidine, pyridazine, triazine, triazole, tetrazole, imidazole, pyrazole, morpholine, thio morpholine, piperidine, piperazine, quinoline, isoquinoline, indole, isoindole, quinoxaline, phthalazine, quinolizine, quinazoline, quinoxaline, naphthyridine, chromene, benzofuran, and benzothiophene.

Preferred are alkyl groups having 1 to 16 carbon atoms, alkenyl groups having 2 to 16 carbon atoms, alkynyl groups having 2 to 16 carbon atoms, aryl groups, alkoxy groups having 2 to 16 carbon atoms, aryloxy groups, alkylthio groups having 2 to 16 carbon atoms, arylthio groups, substituted carbonyl groups having 2 to 17 carbon atoms, substituted oxycarbonyl groups having 2 to 17 carbon atoms, substituted carbonyloxy groups having 2 to 17 carbon atoms, substituted sulfonyl groups having 1 to 16 carbon atoms, mono- or di-substituted carbamoyl groups having 2 to 17 carbon atoms, mono- or di-substituted sulfamoyl groups having 1 to 16 carbon atoms, substituted carbonylamino group having 2 to 17 carbon atoms, mono- or di-substituted ureido groups having 2 to 17 carbon atoms, substituted sulfonylamino groups having 1 to 16 carbon atoms, mono- or di-substituted amino groups having 1 to 16 carbon atoms, a nitro group, a cyano group, substituted silyl groups having 1 to 16 carbon atoms, halogen atoms, and groups given by hetero rings.

More preferred are alkyl groups having 2 to 8 carbon atoms, alkenyl groups having 2 to 8 carbon atoms, alkynyl groups having 2 to 8 carbon atoms, aryl groups, alkoxy groups having 2 to 8 carbon atoms, aryloxy groups, alkylthio groups having 2 to 8 carbon atoms, arylthio groups, substituted carbonyl groups having 2 to 9 carbon atoms, substituted oxycarbonyl groups having 2 to 9 carbon atoms, substituted carbonyloxy groups having 2 to 9 carbon atoms, substituted sulfonyl groups having 1 to 8 carbon atoms, mono- or di-substituted carbamoyl groups having 2 to 9 carbon atoms, mono- or di-substituted sulfamoyl groups having 1 to 8 carbon atoms, substituted carbonylamino group having 2 to 9 carbon atoms, mono- or di-substituted ureido groups having 2 to 9 carbon atoms, substituted sulfonylamino groups having 1 to 8 carbon atoms, mono- or di-substituted amino groups having 1 to 8 carbon atoms, a nitro group, a cyano group, substituted silyl groups having 1 to 8 carbon atoms, halogen atoms, and groups given by hetero rings.

Particularly preferred are alkyl groups having 2 to 8 carbon atoms, alkenyl groups having 2 to 8 carbon atoms, alkynyl groups having 2 to 8 carbon atoms, aryl groups, alkoxy groups having 2 to 8 carbon atoms, aryloxy groups, alkylthio groups having 2 to 8 carbon atoms, arylthio groups, substituted carbonyl groups having 5 to 9 carbon atoms, substituted oxycarbonyl groups having 5 to 9 carbon atoms, substituted carbonyloxy groups having 5 to 9 carbon atoms, substituted sulfonyl groups having 4 to 8 carbon atoms, mono- or di-substituted carbamoyl groups having 5 to 9 carbon atoms, mono- or di-substituted sulfamoyl groups having 4 to 8 carbon atoms, substituted carbonylamino group having 5 to 9 carbon atoms, mono- or di-substituted ureido groups having 5 to 9 carbon atoms, substituted sulfonylamino groups having 4 to 8 carbon atoms, mono- or di-substituted amino groups having 4 to 8 carbon atoms, a nitro group, a cyano group, substituted silyl groups having 1 to 8 carbon atoms, halogen atoms, and groups given by hetero rings.

In the case where the substituent on the ring represented by A is a carbonyl group, since a progress of the side reaction can be prevented at the time of reaction with an organolithium reagent, it is preferable that the ring is substituted with a bulky group having 4 or more carbon atoms, which results in a large steric hindrance, such as a tertiary butyl group.

These substituents each may have another substituent thereon. The kind of the another substituent is not limited in particular, in so far as the substituent does not participate in a reaction. Examples of the another substituent include a lower alkyl group, such as methyl, ethyl, propyl, and butyl groups; an aryl group, such as phenyl and naphthyl groups; and a halogen atom, such as chlorine and fluorine atoms.

As an organolithium reagent used in the present invention, there can be used previously known organolithium compounds. Examples of the organolithium reagent include an alkyl lithium, such as methyl lithium, ethyl lithium, propyl lithium, butyl lithium, pentyl lithium, hexyl lithium, methoxymethyl lithium and ethoxymethyl lithium; an alkenyl lithium, such as vinyl lithium, allyl lithium, propenyl lithium and butenyl lithium; an alkynyl lithium, such as ethynyl lithium, butynyl lithium, pentynyl lithium and hexynyl lithium; and an aralkyl lithium, such as benzyl lithium and phenylethyl lithium. Of these compounds, preferred are alkyl lithium, alkenyl lithium and alkynyl lithium compounds. Specifically, preferred are methyl lithium, ethyl lithium, propyl lithium, n-butyl lithium, sec-butyl lithium, iso-butyl lithium, tert-butyl lithium, n-hexyl lithium, n-octyl lithium, n-decyl lithium, vinyl lithium, allyl lithium, methoxymethyl lithium, benzyl lithium, phenyl lithium, 2-thienyl lithium, and tri(n-butyl)magnesium lithium. More preferred is n-butyl lithium.

The electrophilic compound used in the present invention is not limited in particular, in so far as the compound has a functional group having electron acceptability, namely the compound is able to act as an electrophile. However, preferred are compounds that react with a functional group having a high density of electrons, or with unshared electron pair. In the category of the electrophilic compound herein used, there can be included whole electrophilic compounds that can be used in a halogen-metal exchange reaction using previously known organolithium reagents.

Specifically exemplified electrophilic compounds that can be used in the present invention are halogen, such as chlorine, bromine, and iodine; inorganic substances, such as solid sulfur, sulfur dioxide, and oxygen; carbon dioxide; sulfonic acids, such as methyl ester of trifluoromethylsulfonic acid, and trifluoromethylbenzenesulfonic acid; dimethyl sulfonic acid; nitriles, such as acetonitrile, propionitrile, and benzonitrile; imines, such as benzophenone imine, and acetophenone imine; halogenated silicon compounds, such as chlorotrimethylsilane, chlorodimethylphenylsilane, chlorodimethylsilane, and bromotrimethylsilane; chlorosilane compounds, such as chlorodialkylhydroxysilane; halogenated boron compounds, such as trichloroborane, and tribromoborane; boronic acid esters, such as pinacol boronate, trimethyl boronate, and triisopropyl boronate; boron compounds, such as methoxydiethyl borane, tris(dimethylamino)borane, and bis (pinacolate)diborane; tin compounds, such as dibutyl tin dichloride and diphenyl tin dibromide; aldehydes, such as paraformaldehyde, acetoaldehyde, propionaldehyde, butylaldehyde, acrylaldehyde, benzaldehyde, and nicotine aldehyde; ketones, such as acetone, 2-butanone, benzophenone, acetophenone, DMF, and tert-butyl-4-oxo-1-piperidine carboxylate; esters, such as ethyl chloroformate, phenyl chloroformate, methyl formate, ethyl formate, ethyl acetate, butyl acetate, octyl acetate, phenyl acetate, methyl benzoate, ethyl benzoate, and phenyl benzoate; acid anhydrides, such as acetic anhydride, phthalic anhydride, succinic anhydride, and maleic anhydride; acyl halides, such as acetyl chloride, benzoyl chloride, and 2-pyridine carbonyl chloride; oxyranes, such as oxyrane, and 2-methyl oxyrane; aziridines, such as 6-azabicyclo[3,1,0]hexane, and 7-azabicyclo[4,1,0]heptane; α,β-unsaturated ketones, such as 3-oxo-1,3-diphenyl-1-propene, and 2-methyl-3-oxo-3-diphenyl-1-propene; alkyl halides, such as methyl iodide, ethyl iodide, butyl iodide, methyl bromide, ethyl bromide, hexyl bromide, octyl bromide, 1,2-diiodoethane, 1,2-dibromoethane, 1,6-diiodohexane, 1,8-dibromooctane, and 1,2-dibromocyclopentene; acid imides, such as N-bromosuccinic acid imide, N-iodosuccinic acid imide, N-chlorosuccinic acid imide, and N-bromophthalic acid imide; disulfides, such as dimethyldisulfide, and diphenyldisulfide; phosphines, such as chlorodiphenyl phosphine, and chlorodimethyl phosphine; and phosphine oxides, such as chlorodiphenyl phosphine oxide, and chlorodimethyl phosphine oxide. Of these substances, preferred are chlorotrimethyl silane, benzaldehyde, and DMF.

Preferable specific examples of the compound represented by formula (II), which can be obtained according to the method of the present invention, are shown below, but the present invention should not be construed as being limited to those compounds.

Abbreviations of the compounds set forth below are as follows (the same will be applied to herein).

Me: methyl    Ph: phenyl    Bu: butyl
Et: ethyl     Pr: propyl

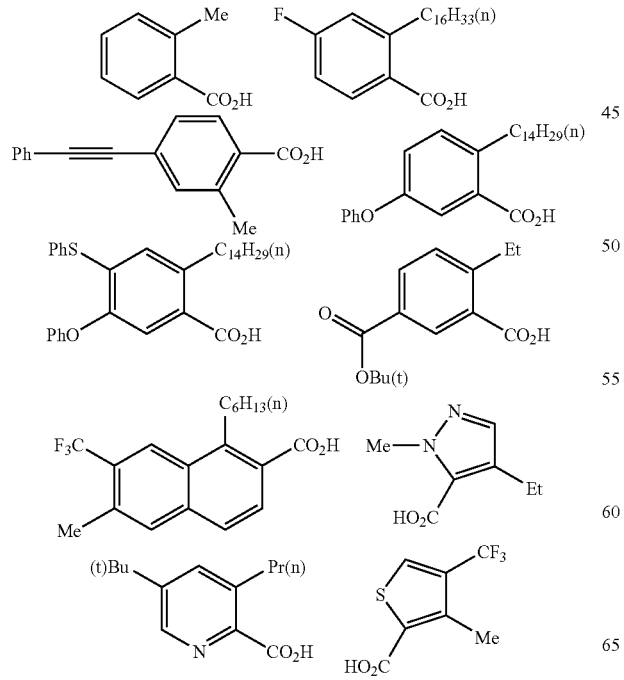

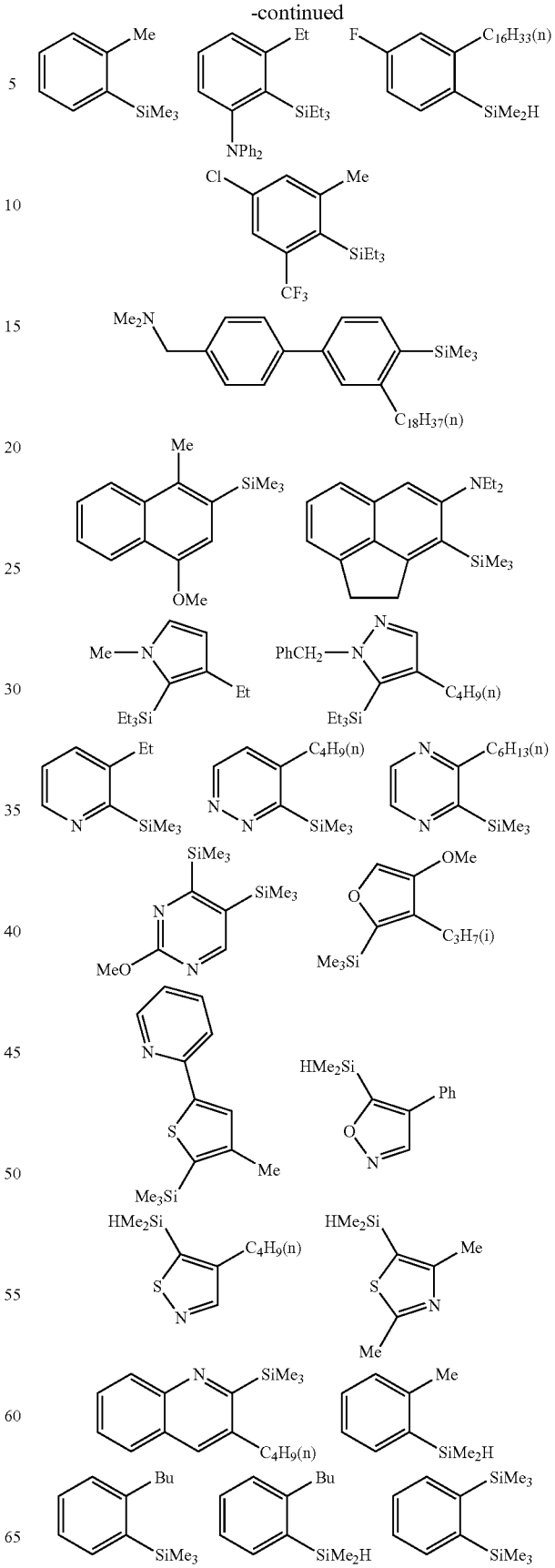

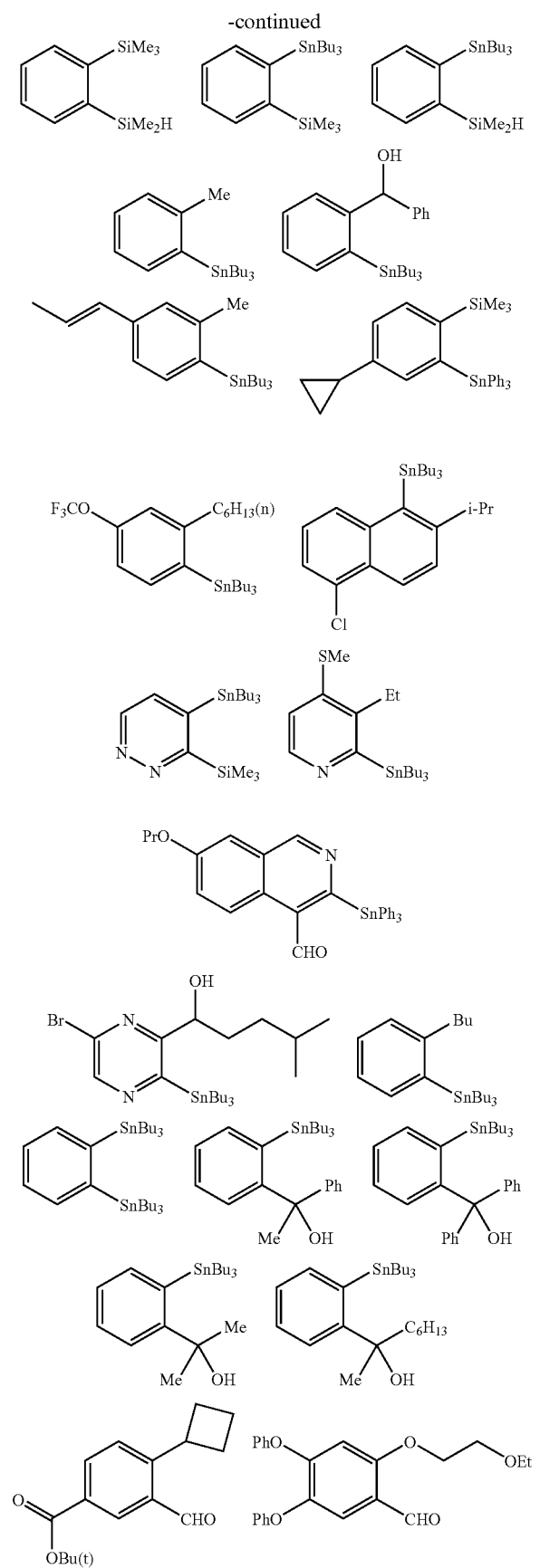
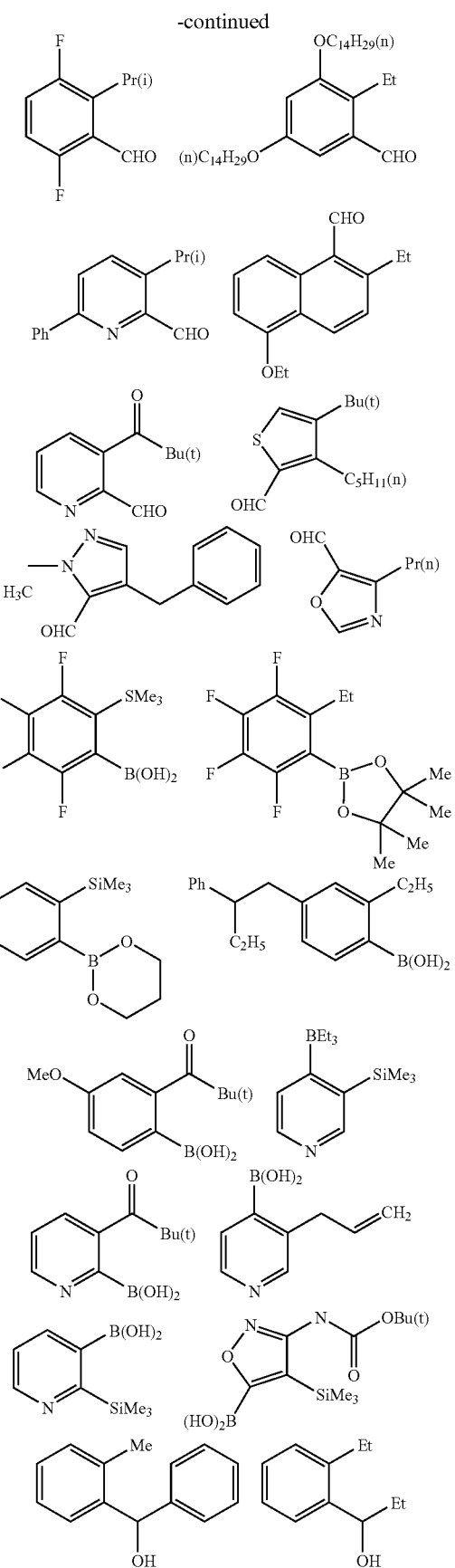

-continued
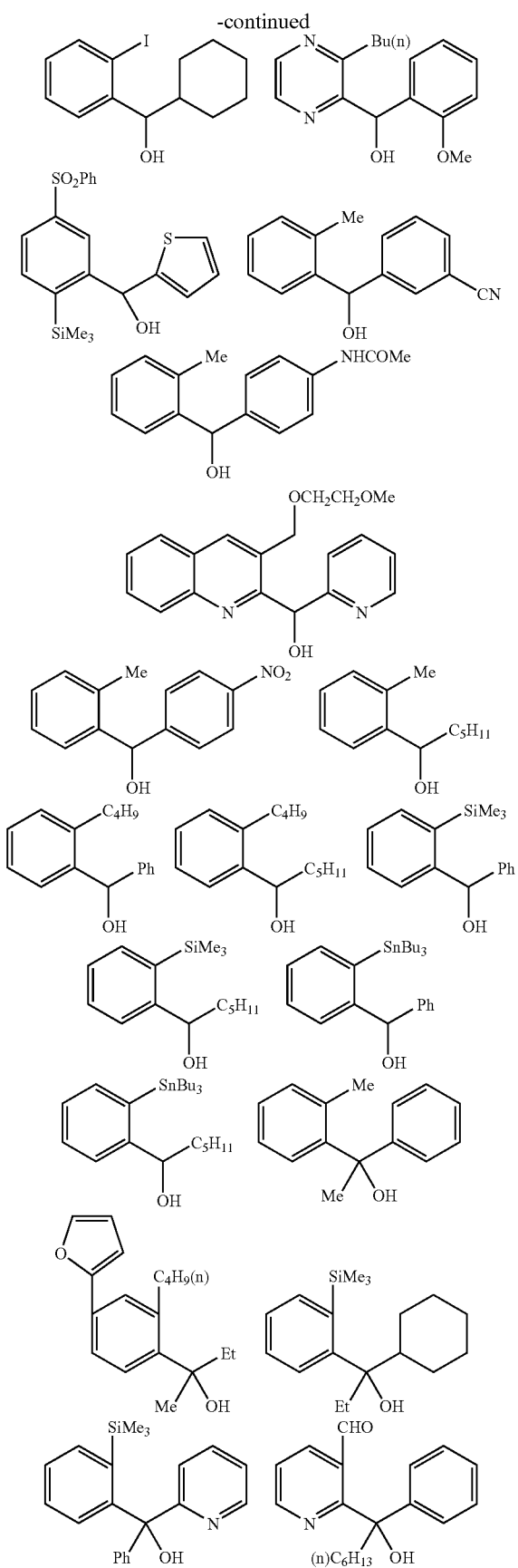
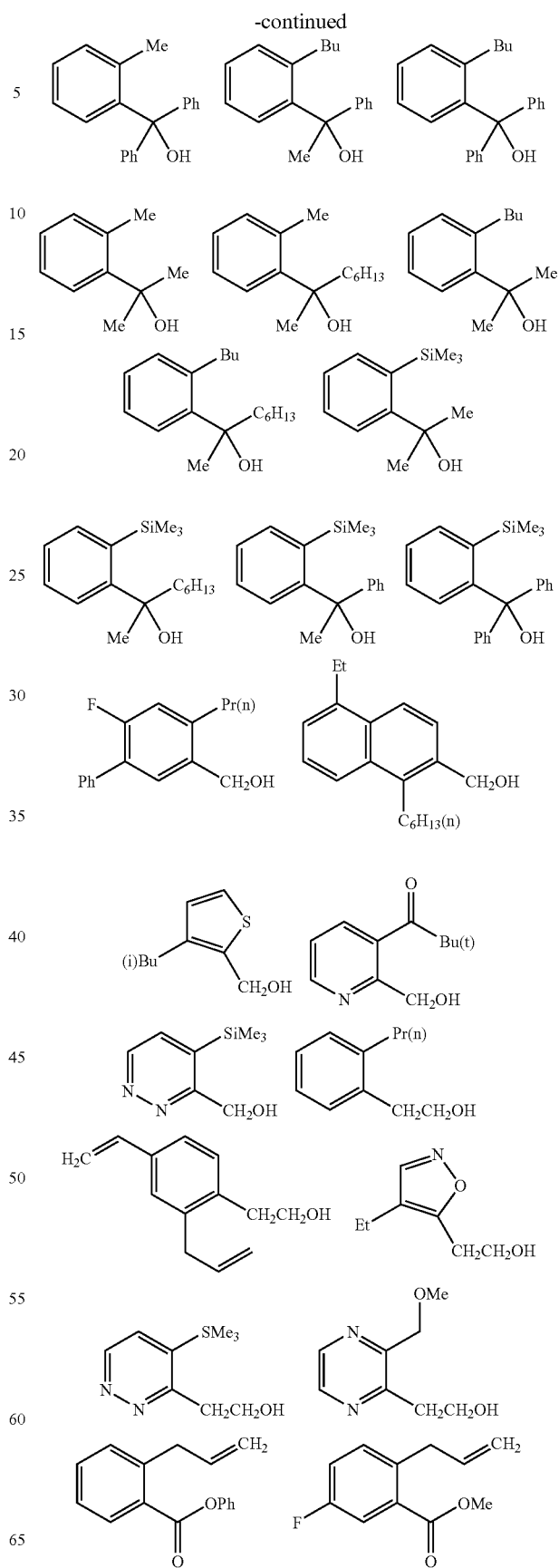

-continued

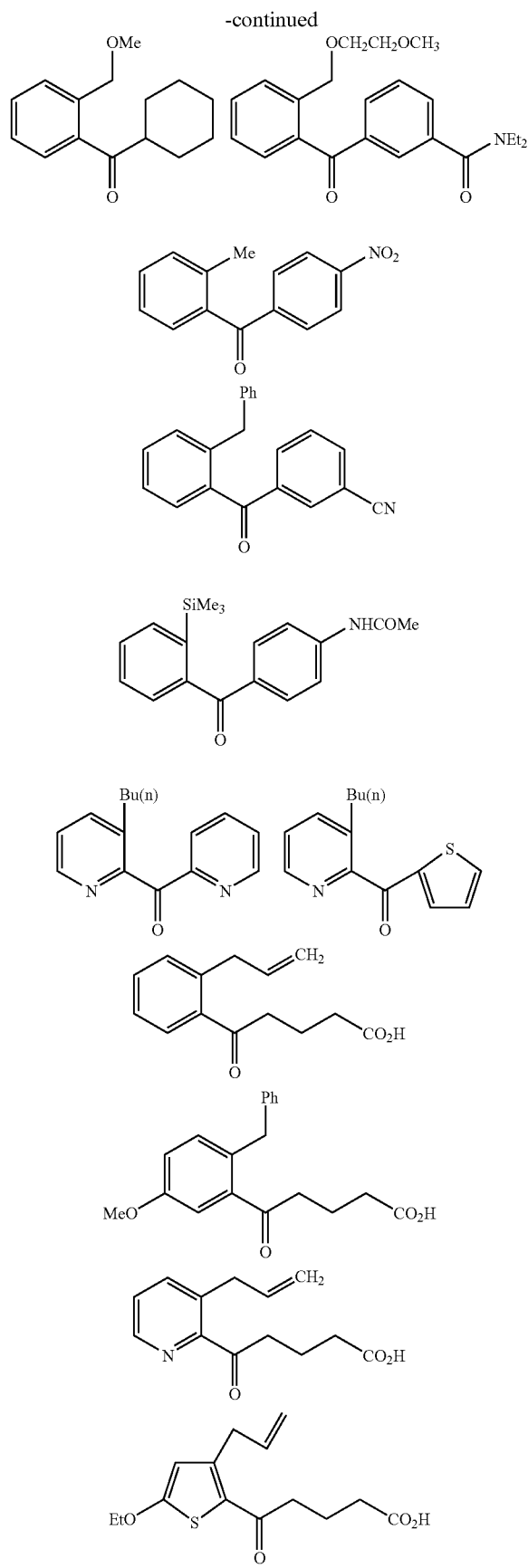

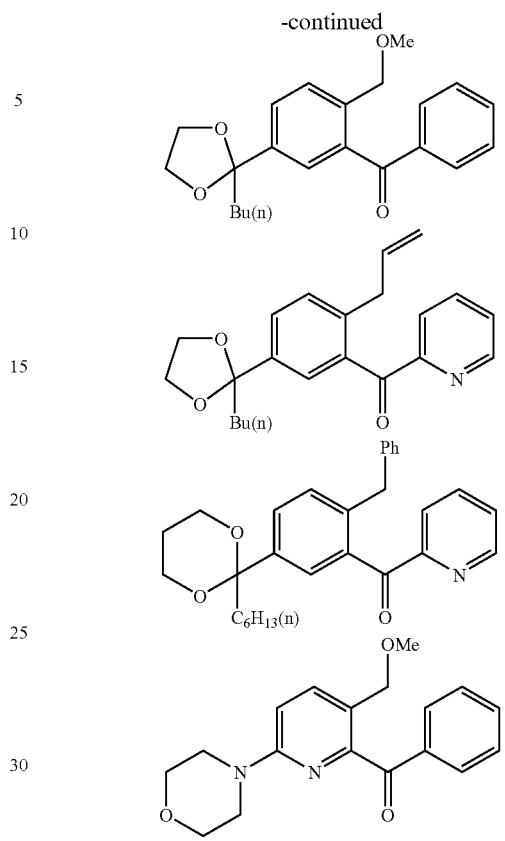

In the producing method of the present invention, it is necessary that the o-dihaloaromatic compound, the organolithium reagent and the electrophilic compound for use in the method are liquid or in the state of solution. Accordingly, if these compounds are not liquid, it is necessary to dissolve them in a solvent that is inert to the reaction before use. As the solvent that can be used for dissolution, there can be used any of known solvents that are used for a halogen-metal exchange reaction. Specifically, any kind of solvents may be used irrespective of polar or nonpolar solvents, as exemplified by aromatic hydrocarbon compounds, such as benzene, toluene, xylene, mesitylene, durene, ethylbenzene, diethylbenzene, isopropylbenzene, diisopropylbenzene, diphenylmethane, chlorobenzene, 1,2-dichlorobenzene, and 1,2,4-trichlorobenzene; polar solvents, such as pyridine, acetonitrile, DMF, N,N-dimethylacetamide, N-methylpyrolidone, and 1,3-dimethyl-2-imidazolidinone; acetates, such as methyl acetate, ethyl acetate, and butyl acetate; alkanes, such as n-pentane, n-hexane, n-heptane, cyclohexane, decane, and paraffin, and perfluoroalkanes; ethers, such as dimethyl ether, diethyl ether, diisopropyl ether, dibutyl ether, dimethoxyethane, petroleum ether, tetrahydrofuran (abbreviated to as THF), dioxane, trioxane, and diglym; ureas, such as N,N-dimethylimidazolidinone; tertiary amines, such as trimethylamine, triethylamine, tributylamine, and N,N,N',N',-tetramethylethylenediamine; and alkane halides, such as methylene chloride, and dichloroethane. Preferred are THF, diethyl ether, diisopropyl ether, dibutyl ether, dimethoxy ethane, toluene, xylene, and 1,3-dimethyl-2-imidazolidinone. More preferred are THF, dibutyl ether, dimethoxy ethane, and toluene. These solvents may be used solely or as a mixture of two or more kinds of solvents. A mixing ratio in the mixture may be arbitrarily set before use. An amount to be used of the solvent is generally in the range of from 1 ml to 10,000 ml, preferably from 300 ml to 6,000 ml, and more preferably from 600 ml to 3,000 ml, per mol of each substance that is a substrate.

In the producing method of the present invention, a chelating agent, such as a tertiary amine may be added in order to activate the organolithium reagent for use in the steps 1 and 3 and the organolithium compound (the compounds (III) or (V) described above). An amount to be used of the chelating agent is generally in the range of from 0.01 mol to 10 mol, preferably from 0.1 mol to 2.0 mol, and more preferably from 0.9 mol to 1.1 mol, per mol of the organolithium reagent and the organolithium compound.

The compound represented by formula (II) that is obtained according to the method of the present invention, can be isolated according to a known method. For example, the compound may be isolated and purified, employing singly an extraction method using an organic solvent, a distillation method, a reprecipitation method using an organic solvent or water or a mixture of an organic solvent and water, or column chromatography, or if necessary, in a proper combination thereof.

The conversion method in the present invention is a modification of known halogen-metal exchange reaction. As the production conditions that can be used for the conversion step according to the present invention, therefore there can be employed any known production conditions including a halogen-metal exchange reaction with an organolithium agent, and purification of the reaction product to be used for reaction with an electrophile, except for a reaction temperature.

The o-disubstituted aromatic compound obtained by the method of the present invention can be used as a synthetic intermediate for various kinds of agricultural chemicals and pharmaceuticals. For example, the compound obtained in the below-described Example 1 is a synthetic intermediate for the production of diaryl iodonium salt, which can be used as a bactericide (U.S. Pat. No. 4,348,525). Besides, the compound obtained in Example 2 is a relatively stable organometal compound, and is used for a C—C coupling reaction as a carbon-anion equivalent substance. Therefore, the compound is very useful in such a field as development of pharmaceuticals and electronic materials. Further, a diphenylcarbinol obtained in Example 4 is useful as a synthetic intermediate for agricultural chemicals and pharmaceuticals. Further, the compound obtained in Example 3 is useful as a synthetic raw material for antidepressant and muscle relaxant. However, the present invention should not be construed as being limited to these uses.

According to the present invention, there can be provided a method of producing a target o-disubstituted aromatic compound with a good efficiency and a high yield, and a high selectivity, using an o-dihaloaromatic compound as a raw material.

Further, according to the present invention, there can be provides a method of producing a target monosubstituted-monohaloaromatic compound with a good efficiency and a high yield and a high selectivity, in an extremely short period of time, using an o-dihaloaromatic compound as a raw material.

According to the method of the present invention, both a lithiation of the o-dihaloaromatic compound and an electrophilic substitution reaction with the thus-lithiated product can be conducted at a temperature of −78° C. or higher that is quite higher than that in a conventional method, and also the substitution reaction of two halogen atoms located at o-positions can be conducted with a good efficiency in succession. Further, during the step of producing the corresponding o-disubstituted aromatic compound starting from an o-dihaloaromatic compound, a benzyne compound can be prevented from being occurred as a by-product, which results in prevention of occurrence of a by-product derived from the benzyne compound. Thus, a target compound can be obtained with a high yield and a high selectivity. The present invention enables not only to perform lithiation and a reaction with an electrophilic compound in the first-half stage, and lithiation and a reaction with an electrophilic compound in the second-half stage in succession, but also to perform the step of the second-half stage at 0° C. Thus, cost of energy for production can be saved. In addition, such the continuous reaction enables to eliminate a working time necessary for a post treatment, thereby to considerably shorten a time period necessary for the entire production. This merit is remarkable from the viewpoint of improvement in productivity.

The present invention will be described in more detail based on the following examples, but the invention is not intended to be limited thereto.

EXAMPLES

Example 1

The present invention was carried out using a microreactor apparatus, as shown in FIG. 1.

A microsystem composed of four T-shaped micromixers (M1, M2, M3 and M4) and four microtube reactors (R1, R2, R3 and R4) was used. The M1, R1, M2 and R2 were dipped in a cooling bath (−78° C.), and the M3, R3, M4 and R4 were dipped in a cooling bath (0° C.). A reaction solution flowed from R4 was cooled at 0° C., and was collected in a flask. A solution of o-dibromobenzene (0.27 M) in THF (flow rate: 6 mL/min, 1.62 mmol/min) and a solution of n-BuLi (1.5 M) in n-hexane (flow rate: 1.2 mL/min, 1.8 mmol/min) were introduced to the first T-shaped mixer M1 (inner diameter: 250 μm) by using syringe pumps. A solution of methyl trifluoromethanesulfonate (MeOTf) (0.65 M) in THF (flow rate: 3 mL/min, 1.95 mmol/min) was introduced to the second T-shaped mixer M2 (inner diameter: 500 μm). A solution of n-BuLi (1.5 M) in n-hexane (flow rate: 1.8 mL/min, 2.7 mmol/min) was introduced to the third T-shaped mixer M3 (inner diameter: 500 μm). A solution of chlorotrimethylsilane (1.62 M) in THF (flow rate: 3 mL/min, 4.86 mmol/min) was introduced to the fourth T-shaped mixer M4 (inner diameter: 500 μm). The residence time of the tube reactor R1 (inner diameter: 500 μm, length=50 cm) was 0.82 second. The residence time of the tube reactor R2 (inner diameter: 1,000 μm, length=150 cm) was 6.93 second. The residence time of the tube reactor R3 (inner diameter: 1,000 μm, length=12.5 cm) was 0.49 second. The residence time of the tube reactor R4 (inner diameter: 1,000 μm, length=150 cm) was 1.57 second. After passing through R4, an aliquot of the product solution was taken (15 sec) and was stirred for 1 hour in ice bath (0° C.). As a result of the product solution was analyzed by GC (column, CBP1; 0.25 mm×25 m; initial oven temperature, 50° C.; rate of temperature increase, 10° C./min), trimethyl (o-tolyl)silane (GC retention time: 13.5 min) was obtained in 67% yield. $^1$H NMR (400 MHz, CDCl$_3$) δ: 0.32 (s, 9H), 2.45 (s, 3H), 7.14 (tt, J=7.6, 0.4 Hz, 2H), 7.25 (t, J=7.2 Hz, 1H), 7.44 (d, J=6.8 Hz, 1H); $^{13}$C NMR (100 MHz) δ: 0.0, 23.1, 124.7, 129.0, 129.6, 134.1, 138.2, 143.3. The thus-obtained spectral data were identical to those described in a literature.

Reaction components used in this Example and the results were shown in Table 1 set forth below.

Example 2

The microreactor apparatus same as shown in FIG. 1 was used.

A microsystem composed of four T-shaped micromixers (M1, M2, M3 and M4) and four microtube reactors (R1, R2, R3 and R4) was used. The M1, R1, M2 and R2 were dipped in a cooling bath (−78° C.), and the M3, R3, M4 and R4 were dipped in a cooling bath (0° C.). A reaction solution flowed from R4 was cooled at 0° C., and was collected in a flask. A solution of o-dibromobenzene (0.27 M) in THF (flow rate: 6 mL/min, 1.62 mmol/min) and a solution of n-BuLi (1.5 M) in n-hexane (flow rate: 1.2 mL/min, 1.8 mmol/min) were introduced to the first T-shaped mixer M1 (inner diameter: 250 μm) by using syringe pumps. A solution of methyl trifluoromethanesulfonate (0.65 M) in THF (flow rate: 3 mL/min, 1.95 mmol/min) was introduced to the second T-shaped mixer M2 (inner diameter: 500 μm). A solution of n-BuLi (1.5 M) in n-hexane (flow rate: 1.8 mL/min, 2.7 mmol/min) was introduced to the third T-shaped mixer M3 (inner diameter: 500 μm). A solution of chlorotributylstannane (1.62 M) in THF (flow rate: 3 mL/min, 4.86 mmol/min) was introduced to the fourth T-shaped mixer M4 (inner diameter: 500 μm). The residence time of the tube reactor R1 (inner diameter: 500 μm, length=50 cm) was 0.82 second. The residence time of the tube reactor R2 (inner diameter: 1,000 μm, length=150 cm) was 6.93 second. The residence time of the tube reactor R3 (inner diameter: 1,000 μm, length=12.5 cm) was 0.49 second. The residence time of the tube reactor R4 (inner diameter: 1,000 μm, length=150 cm) was 1.57 second. After passing through R4, an aliquot of the product solution was taken (15 sec) and was stirred for 1 hour in ice bath (0° C.). As a result of the product solution was analyzed by GC (column, CBP1; 0.25 mm×25 m; initial oven temperature, 50° C.; rate of temperature increase, 10° C./min), tributyl(o-tolyl)stannane (GC retention time: 25.3 min) was obtained in 62% yield. $^1$H NMR (400 MHz, CDCl$_3$) δ: 0.89 (t, J=7.2 Hz, 9H), 1.04-1.09 (m, 6H), 1.26-1.38 (m, 6H), 1.44-1.56 (m, 6H), 2.38 (s, 3H), 7.08-7.39 (m, 4H); $^{13}$C NMR (100 MHz) δ: 10.2, 13.8, 25.1, 27.5, 29.3, 124.7, 128.1, 128.7, 136.4, 141.8, 144.4. HRMS (EI) m/z: calcd. for $C_{15}H_{25}Sn$ ($M^+$-$C_4H_9$) 325.0978, found 325.0979. The thus-obtained spectral data were identical to those described in a literature. Reaction components used in this Example and the results were shown in Table 1 set forth below.

Example 3

The microreactor apparatus same shown in FIG. 1 was used.

A microsystem composed of four T-shaped micromixers (M1, M2, M3 and M4) and four microtube reactors (R1, R2, R3 and R4) was used. The M1, R1, M2 and R2 were dipped in a cooling bath (−78° C.), and the M3, R3, M4 and R4 were dipped in a cooling bath (0° C.). A reaction solution flowed from R4 was cooled at 0° C., and was collected in a flask. A solution of o-dibromobenzene (0.27 M) in THF (flow rate: 6 mL/min, 1.62 mmol/min) and a solution of n-BuLi (1.5 M) in n-hexane (flow rate: 1.2 mL/min, 1.8 mmol/min) were introduced to the first T-shaped mixer M1 (inner diameter: 250 μm) by using syringe pumps. A solution of methyl trifluoromethanesulfonate (0.65 M) in THF (flow rate: 3 mL/min, 1.95 mmol/min) was introduced to the second T-shaped mixer M2 (inner diameter: 500 μm). A solution of n-BuLi (1.5 M) in n-hexane (flow rate: 1.8 mL/min, 2.7 mmol/min) was introduced to the third T-shaped mixer M3 (inner diameter: 500 μm). A solution of benzaldehyde (1.62 M) in THF (flow rate: 3 mL/min, 4.86 mmol/min) was introduced to the fourth T-shaped mixer M4 (inner diameter: 500 μm). The residence time of the tube reactor R1 (inner diameter: 500 μm, length=50 cm) was 0.82 second. The residence time of the tube reactor R2 (inner diameter: 1,000 μm, length=150 cm) was 6.93 second. The residence time of the tube reactor R3 (inner diameter: 1,000 μm, length=12.5 cm) was 0.49 second. The residence time of the tube reactor R4 (inner diameter: 1,000 μm, length=150 cm) was 1.57 second. After passing through R4, an aliquot of the product solution was taken (15 sec) and was stirred for 1 hour in ice bath (0° C.). As a result of the product solution was analyzed by GC (column, CBP1; 0.25 mm×25 m; initial oven temperature, 50° C.; rate of temperature increase, 10° C./min), phenyl-o-tolylmethanol (GC retention time: 21.8 min) was obtained in 61% yield. $^1$H NMR (400 MHz, CDCl$_3$) δ: 2.27 (s, 3H), 6.02 (s, 1H), 7.12-7.36 (m, 8H), 7.52 (dd, J=5.6, 1.6 Hz, 1H); $^{13}$C NMR (100 MHz) δ: 19.5, 73.4, 126.0, 126.2, 127.0, 127.40, 127.43, 128.3, 130.4, 135.2, 141.3, 142.7. The thus-obtained spectral data were identical to those described in a literature. Reaction components used in this Example and the results were shown in Table 1 set forth below.

Example 4

The microreactor apparatus same as shown in FIG. 1 was used.

A microsystem composed of four T-shaped micromixers (M1, M2, M3 and M4) and four microtube reactors (R1, R2, R3 and R4) was used. The M1, R1, M2 and R2 were dipped in a cooling bath (−78° C.), and the M3, R3, M4 and R4 were dipped in a cooling bath (0° C.). A reaction solution flowed from R4 was cooled at 0° C., and was collected in a flask. A solution of o-dibromobenzene (0.27 M) in THF (flow rate: 6 mL/min, 1.62 mmol/min) and a solution of n-BuLi (1.5 M) in n-hexane (flow rate: 1.2 mL/min, 1.8 mmol/min) were introduced to the first T-shaped mixer M1 (inner diameter: 250 μm) by using syringe pumps. A solution of methyl trifluoromethanesulfonate (0.65 M) in THF (flow rate: 3 mL/min, 1.95 mmol/min) was introduced to the second T-shaped mixer M2 (inner diameter: 500 μm). A solution of n-BuLi (1.5 M) in n-hexane (flow rate: 1.8 mL/min, 2.7 mmol/min) was introduced to the third T-shaped mixer M3 (inner diameter: 500 μm). A solution of acetophenone (1.62 M) in THF (flow rate: 3 mL/min, 4.86 mmol/min) was introduced to the fourth T-shaped mixer M4 (inner diameter: 500 μm). The residence time of the tube reactor R1 (inner diameter: 500 μm, length=50 cm) was 0.82 second. The residence time of the tube reactor R2 (inner diameter: 1,000 μm, length=150 cm) was 6.93 second. The residence time of the tube reactor R3 (inner diameter: 1,000 μm, length=12.5 cm) was 0.49 second. The residence time of the tube reactor R4 (inner diameter: 1,000 μm, length=150 cm) was 1.57 second. After passing through R4, an aliquot of the product solution was taken (15 sec) and was stirred for 1 hour in ice bath (0° C.). As a result of the product solution was analyzed by GC (column, CBP1; 0.25 mm×25 m; initial oven temperature, 50° C.; rate of temperature increase, 10° C./min), 1-phenyl-1-(o-tolyl)ethanol (GC retention time: 21.7 min) was obtained in 53% yield. $^1$H NMR (400 MHz, CDCl$_3$) δ: 1.85 (s, 3H), 1.94 (s, 3H), 2.29 (br s, 1H), 7.04 (dd, J=6.8, 1.6 Hz, 1H), 7.10-7.28 (m, 7H), 7.61 (dd, J=7.2, 2.0 Hz, 1H); $^{13}$C NMR (100 MHz) δ: 21.4, 32.1, 76.6, 125.08, 125.12, 125.7, 126.3, 127.4, 127.8, 132.2, 136.9, 144.3, 147.7. The thus-obtained spectral data were identical to those described in a literature. Reaction components used in this Example and the results were shown in Table 1 set forth below.

Example 5

The microreactor apparatus same as shown in FIG. 1 was used.

A microsystem composed of four T-shaped micromixers (M1, M2, M3 and M4) and four microtube reactors (R1, R2, R3 and R4) was used. The M1, R1, M2 and R2 were dipped in a cooling bath (−78° C.), and the M3, R3, M4 and R4 were dipped in a cooling bath (0° C.). A reaction solution flowed from R4 was cooled at 0° C., and was collected in a flask. A solution of o-dibromobenzene (0.27 M) in THF (flow rate: 6 mL/min, 1.62 mmol/min) and a solution of n-BuLi (1.5 M) in n-hexane (flow rate: 1.2 mL/min, 1.8 mmol/min) were introduced to the first T-shaped mixer M1 (inner diameter: 250 μm) by using syringe pumps. A solution of benzaldehyde (0.65 M) in THF (flow rate: 3 mL/min, 1.95 mmol/min) was introduced to the second T-shaped mixer M2 (inner diameter: 500 μm). A solution of n-BuLi (1.5 M) in n-hexane (flow rate: 1.8 mL/min, 2.7 mmol/min) was introduced to the third T-shaped mixer M3 (inner diameter: 500 μm). A solution of chlorotrimethylsilane (1.62 M) in THF (flow rate: 3 mL/min, 4.86 mmol/min) was introduced to the fourth T-shaped mixer M4 (inner diameter: 500 μm). The residence time of the tube reactor R1 (inner diameter: 500 μm, length=50 cm) was 0.82 second. The residence time of the tube reactor R2 (inner diameter: 1,000 μm, length=150 cm) was 6.93 second. The residence time of the tube reactor R3 (inner diameter: 1,000 μm, length=12.5 cm) was 0.49 second. The residence time of the tube reactor R4 (inner diameter: 1,000 μm, length=150 cm) was 1.57 second. After passing through R4, an aliquot of the product solution was taken (15 sec) and was stirred for 1 hour in ice bath (0° C.). As a result of the product solution was analyzed by GC (column, CBP1; 0.25 mm×25 m; initial oven temperature, 50° C.; rate of temperature increase, 10° C./min), phenyl(2-(trimethylsilyl)phenyl)methanol (GC retention time: 23.9 min) was obtained in 74% yield. $^1$H NMR (400 MHz, CDCl$_3$) δ: 0.56 (s, 9H), 2.67 (br s, 1H), 6.28 (s, 1H), 7.35-7.49 (m, 8H), 7.71-7.74 (m, 1H); $^{13}$C NMR (100 MHz) δ: 0.9, 74.5, 126.4, 126.8, 127.0, 127.8, 127.9, 129.6, 134.2, 138.4, 143.5, 149.0. HRMS (EI) m/z: calcd. for C$_{15}$H$_{17}$OSi (M$^+$-CH$_3$) 241.1049, found 241.1049. Reaction components used in this Example and the results were shown in Table 1 set forth below.

Example 6

The microreactor apparatus same as shown in FIG. 1 was used.

A microsystem composed of four T-shaped micromixers (M1, M2, M3 and M4) and four microtube reactors (R1, R2, R3 and R4) was used. The M1, R1, M2 and R2 were dipped in a cooling bath (−78° C.), and the M3, R3, M4 and R4 were dipped in a cooling bath (0° C.). A reaction solution flowed from R4 was cooled at 0° C., and was collected in a flask. A solution of o-dibromobenzene (0.27 M) in THF (flow rate: 6 mL/min, 1.62 mmol/min) and a solution of n-BuLi (1.5 M) in n-hexane (flow rate: 1.2 mL/min, 1.8 mmol/min) were introduced to the first T-shaped mixer M1 (inner diameter: 250 μm) by using syringe pumps. A solution of benzaldehyde (0.65 M) in THF (flow rate: 3 mL/min, 1.95 mmol/min) was introduced to the second T-shaped mixer M2 (inner diameter: 500 μm). A solution of n-BuLi (1.5 M) in n-hexane (flow rate: 1.8 mL/min, 2.7 mmol/min) was introduced to the third T-shaped mixer M3 (inner diameter: 500 μm). A solution of chlorotributylstannane (1.62 M) in THF (flow rate: 3 mL/min, 4.86 mmol/min) was introduced to the fourth T-shaped mixer M4 (inner diameter: 500 μm). The residence time of the tube reactor R1 (inner diameter: 500 μm, length=50 cm) was 0.82 second. The residence time of the tube reactor R2 (inner diameter: 1,000 μm, length=150 cm) was 6.93 second. The residence time of the tube reactor R3 (inner diameter: 1,000 μm, length=12.5 cm) was 0.49 second. The residence time of the tube reactor R4 (inner diameter: 1,000 μm, length=150 cm) was 1.57 second. After passing through R4, an aliquot of the product solution was taken (15 sec) and was stirred for 1 hour in ice bath (0° C.). After finishing the reaction, the solution was concentrated, then the residue was subjected to silica gel column chromatography (hexane) to refine, phenyl (2-(tributylstannanyl)phenyl)methanol was obtained as colorless oil in 58% yield, 111.0 mg. $^1$H NMR (400 MHz, CDCl$_3$) δ: 0.86 (t, J=7.6 Hz, 9H), 1.01-1.05 (m, 6H), 1.25-1.35 (m, 6H), 1.45-1.53 (m, 6H), 2.11 (d, J=7.6 Hz, 1H), 5.73 (d, J=7.6 Hz, 1H), 7.16-7.34 (m, 8H), 7.47-7.51 (m, 1H); $^{13}$C NMR (100 MHz, CDCl$_3$) δ: 11.0, 13.8, 27.5, 29.3, 78.0, 126.9, 127.0, 127.26, 127.32, 128.2, 128.3, 136.7, 141.8, 143.4, 149.6. HRMS (EI) m/z: calcd. for C$_{21}$H$_{29}$OSn (M$^+$-C$_4$H$_9$) 417.1240, found 417.1239. Reaction components used in this Example and the results were shown in Table 1 set forth below.

TABLE 1

| No. | Electrophile$_{(E^1)}$ | Electrophile$_{(E^2)}$ | Product | Yield (%) |
|---|---|---|---|---|
| 1 | MeOTf | Me$_3$SiCl | 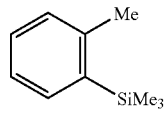 | 67 |
| 2 | MeOTf | Bu$_3$SnCl | 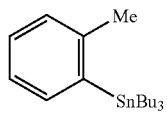 | 62 |

TABLE 1-continued

| No. | Electrophile$_{(E^1)}$ | Electrophile$_{(E^2)}$ | Product | Yield (%) |
|---|---|---|---|---|
| 3 | MeOTf | PhCHO | 2-methylphenyl(phenyl)methanol | 61 |
| 4 | MeOTf | PhC(O)Me | 1-(2-methylphenyl)-1-phenylethanol | 53 |
| 5 | PhCHO | Me$_3$SiCl | (2-(trimethylsilyl)phenyl)(phenyl)methanol | 74 |
| 6 | PhCHO | Bu$_3$SnCl | (2-(tributylstannyl)phenyl)(phenyl)methanol | 58 |

Comparative Example 1 and Comparative Example 2

Synthesis of trimethyl(o-tolyl)silane was tried to conduct in the same as in Example 1, except that the step 3 and the step 4 were performed according to the following reaction scheme by a batch manner as described in detail below. The results are shown in the following Table 2.

TABLE 2 o-bromotoluene $\xrightarrow[\text{T (° C.) 30 min}]{\text{n-BuLi (1.65eq)}}$ $\xrightarrow[\text{T' (° C.), 1 hour}]{\text{Me}_3\text{SiCl (3eq)}}$ o-trimethylsilyltoluene + o-butyltoluene (by-product)

| | T (° C.) | T' (° C.) | Yield (%) | by-product (%) |
|---|---|---|---|---|
| Comparative example 1 | 0 | 0 | 4 | 91 |
| Comparative example 2 | −78 | −78 | Quantitatively | 0 |

In Comparative Example 1, synthesis was carried out as described below.

In a 10 ml volume double neck flask substituted with argon gas, was laid 2 ml of a THF solution containing 0.32 mmol/L of o-bromotoluene obtained in the step 2 of Example 1, followed by cooling at 0° C. in an atmosphere of argon gas. To the solution, while stirring using a magnetic stirrer, 0.34 ml of a n-hexane containing 1.58 mol/L of n-butyl lithium was slowly drop wise added and stirred at 0° C. for 30 min. Subsequently, 0.59 ml of a THF solution containing 0.96 mmol/L of chlorotrimethylsilane was slowly drop wise added and stirred at 0° C. for 60 min. After reaction, the resulting solution was analyzed using GC (CBP column 1; 0.25 mm×25 m; starting temperature 50° C.; rate of temperature increase 10° C./min). As a result, o-trimethylsilyltoluene was obtained in yield of 4%. In addition, o-butyltoluene was obtained as a by-product in yield of 91%.

In Comparative Example 2, synthesis was carried out as described below.

In a 10 ml volume double neck flask substituted with argon gas, was laid 2 ml of a THF solution containing 0.32 mmol/L of o-bromotoluene obtained in the step 2 of Example 1, followed by cooling at −78° C. in an atmosphere of argon gas. To the solution, while stirring using a magnetic stirrer, 0.34 ml of a n-hexane containing 1.58 mol/L of n-butyl lithium was slowly drop wise added and stirred at −78° C. for 30 min. Subsequently, 0.59 ml of a THF solution containing 0.96 mmol/L of chlorotrimethylsilane was slowly drop wise added and stirred at −78° C. for 60 min. After reaction, the resulting solution was analyzed using GC (CBP column 1; 0.25 mm×25 m; starting temperature 50° C.; rate of temperature increase 10° C./min). As a result, o-trimethylsilyltoluene was obtained with a quantitative yield.

The followings are apparent from the results of Comparative Example 1 and Comparative Example 2 shown in Table 2 and the results of the above Examples set forth above.

Among 4 stage reactions of the steps 1 to 4 connected to each other, o-bromo lithium compound that is a product of the first stage has so poor stability to heat, that it is necessary to perform the reaction at −110° C. that is an extremely low temperature in a batch process that is a previous synthesis technology. Moreover, such the cooling condition of −78° C. is also necessary in a lithiation reaction of the third stage and an electrophilic exchange reaction of the lithiated product of the fourth stage. In addition, the batch process necessitates totally 90 minutes including 30 minutes for the lithiation reaction in the third stage and 60 minutes for the electrophilic exchange reaction in the fourth stage. Consequently, the reaction time was incomparably prolonged to the reaction time of a second order in Example 1.

Furthermore, the batch process necessitates increase of the temperature by heating to room temperature and a post treatment such as separation in order to isolate the product. Totally, a great waste of energy occurs in the batch process.

In contrast, it is possible in each of the Examples of the present invention not only to perform lithiation and a reaction with an electrophilic compound in the preceding stage and lithiation and a reaction with an electrophilic compound in the latter stage in succession, but also to perform the steps 3 and 4 of the latter stage at 0° C. Thereby, a cost of energy for production can be saved. In addition, such the continuous reaction enables to eliminate a working time necessary for a post treatment, thereby to considerably reduce a time necessary for production. This merit is very significant from a view of improvement in productivity.

Example 7

$E_1$=H and $X_2$=Br in Formula (IV)

Figure 2:
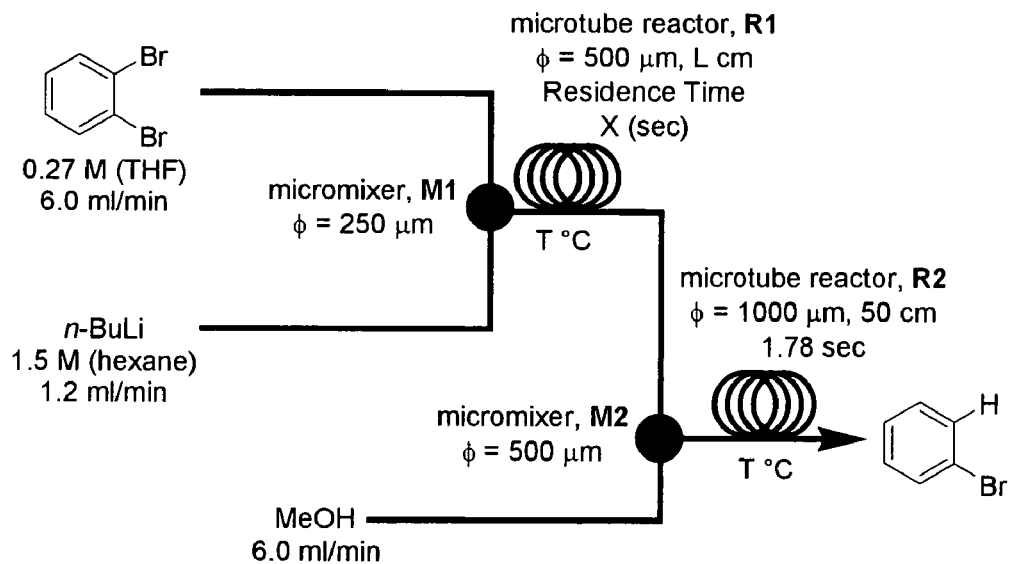
FIG. 2. is an explanatory view that shows a symbolic view of the microreactor apparatuses used in Example 7, accompanied with reaction conditions.

The present invention was carried out using a microreactor apparatus, as shown in FIG. 2.

A microsystem composed of two T-shaped micromixers (M1 and M2) and two microtube reactors (R1 and R2) was used. The whole microsystem was dipped in a cooling bath (T ° C.). A solution of o-dibromobenzene (0.27 M) in THF (flow rate: 6 mL/min, 1.62 mmol/min) and a solution of n-BuLi (1.5 M) in n-hexane (flow rate: 1.2 mL/min, 1.8 mmol/min) were introduced to the first T-shaped mixer M1 (inner diameter: 250 μm) by using syringe pumps. The resulting solution was passed through the microtube reactor R1 and was introduced to the second T-shaped mixer M2 (inner diameter: 500 μm). The solution was quenched with undiluted methanol (MeOH) (flow rate: 6 mL/min) and was introduced to the M2. The residence time of the tube reactor R1 (inner diameter: 500 μm, length=L cm) was X second. The residence time of the tube reactor R2 (inner diameter: 1,000 μm, length=50 cm) was 1.78 second. After finishing the reaction, an aliquot of the product solution was taken (15 sec) and was analyzed by GC (column, CBP1; 0.25 mm×25 m; initial oven temperature, 50° C.; rate of temperature increase, 10° C./min). Table 3 shows the results obtained by the tests that were carried out changing the above-described temperature (T ° C.), length of the first tube reactor R1 (L cm) and residence time (X sec).

TABLE 3

| T (° C.) | L (cm) | X (sec) | Yield (%) |
|---|---|---|---|
| −85 | 6.0 | 0.10 | 24 |
|  | 12.5 | 0.21 | 16 |
|  | 25.0 | 0.41 | 20 |
|  | 50.0 | 0.82 | 44 |
|  | 100.0 | 1.64 | 51 |
| −78 | 6.0 | 0.10 | 29 |
|  | 12.5 | 0.21 | 33 |
|  | 25.0 | 0.41 | 37 |
|  | 50.0 | 0.82 | 74 |
|  | 100.0 | 1.64 | 61 |

TABLE 3-continued

| T (° C.) | L (cm) | X (sec) | Yield (%) |
|---|---|---|---|
| −70 | 3.0 | 0.05 | 41 |
|  | 6.0 | 0.10 | 42 |
|  | 12.5 | 0.21 | 52 |
|  | 25.0 | 0.41 | 59 |
|  | 50.0 | 0.82 | 70 |
|  | 100.0 | 1.64 | 47 |
| −65 | 3.0 | 0.05 | 41 |
|  | 6.0 | 0.10 | 45 |
|  | 12.5 | 0.21 | 40 |
|  | 25.0 | 0.41 | 35 |
| −60 | 3.0 | 0.05 | 31 |
|  | 6.0 | 0.10 | 15 |
|  | 12.5 | 0.21 | 14 |
|  | 25.0 | 0.41 | 5 |
|  | 50.0 | 0.82 | 7 |

Example 8

$E_1$=Me and $X_2$=Br in Formula (IV)

Figure 3:
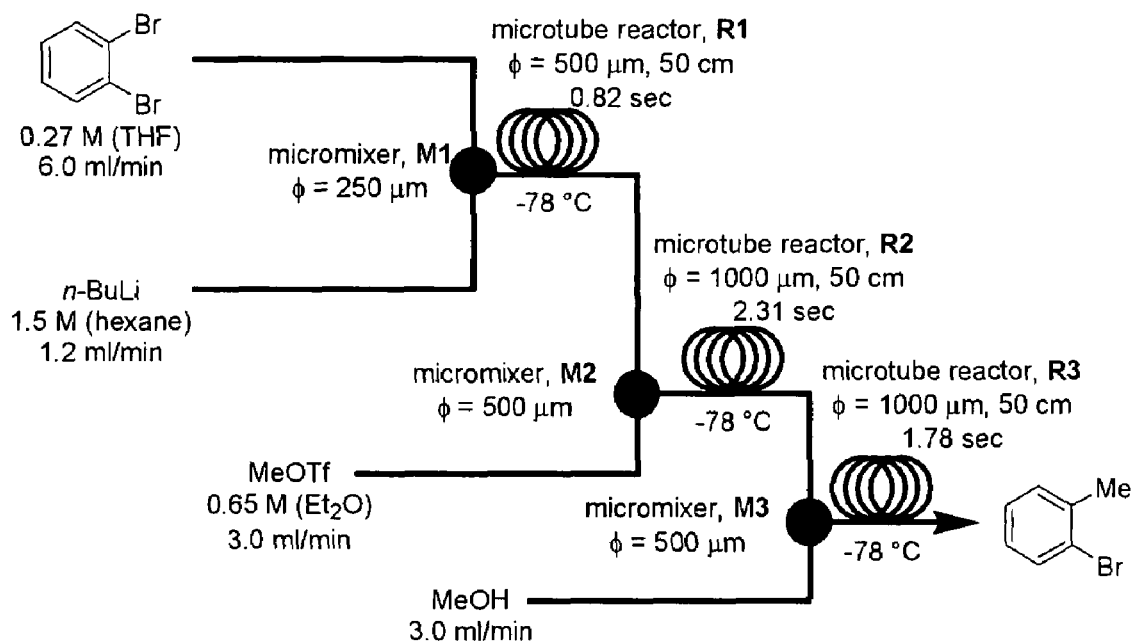
FIG. 3 is an explanatory view that shows a symbolic view of the microreactor apparatuses used in Example 8, accompanied with reaction conditions.

The present invention was carried out using a microreactor apparatus, as shown in FIG. 3.

A microsystem composed of three T-shaped micromixers (M1, M2 and M3) and two microtube reactors (R1 and R2) was used. The whole microsystem was dipped in a cooling bath (−78° C.). A solution of o-dibromobenzene (0.27 M) in THF (flow rate: 6 mL/min, 1.62 mmol/min) and a solution of n-BuLi (1.5 M) in n-hexane (flow rate: 1.2 mL/min, 1.8 mmol/min) were introduced to the first T-shaped mixer M1 (inner diameter: 250 μm) by using syringe pumps. The resulting solution was passed through the tube reactor R1 and was mixed with methyl trifluoromethanesulfonate (MeOTf) (0.65 M) in $Et_2O$ (flow rate: 3 mL/min, 1.95 mmol/min) in the second T-shaped mixer M2 (inner diameter: 500 μm). The resulting solution was passed through the tube reactor R2 and was introduced to the third T-shaped mixer M3 (inner diameter: 500 μm), where the solution was quenched with methanol (neat, flow rate=3.0 mmol/min). The residence time of the tube reactor R1 (inner diameter: 500 μm, length=50 cm) was 0.82 second. The residence time of the tube reactor R2 (inner diameter: 1,000 μm, length=50 cm) was 2.31 second. After finishing the reaction, an aliquot of the product solution was taken (15 sec) and was analyzed by GC (column, CBP1; 0.25 mm×25 m; initial oven temperature, 50° C.; rate of temperature increase, 10° C./min). As a result, o-bromotoluene (GC retention time: 11.5 min) was obtained in 79% yield.

Example 9

$E_1$=SiHMe$_2$ and $X_2$=Br in Formula (IV)

The present invention was carried out using a microreactor apparatus, as shown in FIG. 3.

A microsystem composed of three T-shaped micromixers (M1, M2 and M3) and two microtube reactors (R1 and R2) was used. The whole microsystem was dipped in a cooling bath (−78° C.). A solution of o-dibromobenzene (0.27 M) in THF (flow rate: 6 mL/min, 1.62 mmol/min) and a solution of n-BuLi (1.5 M) in n-hexane (flow rate: 1.2 mL/min, 1.8 mmol/min) were introduced to the first T-shaped mixer M1 (inner diameter: 250 μm) by using syringe pumps. The resulting solution was passed through the tube reactor R1 and was mixed with chlorodimethylsilane (HMe$_2$SiCl) (0.65 M) in THF (flow rate: 3 mL/min, 1.95 mmol/min) in the second T-shaped mixer M2 (inner diameter: 500 μm). The solution was introduced to the third T-shaped mixer M3 (inner diameter: 500 μm), where the solution was quenched with methanol (neat, flow rate=3.0 mmol/min). The residence time of the tube reactor R1 (inner diameter: 500 μm, length=50 cm) was 0.82 second. The residence time of the tube reactor R2 (inner diameter: 1,000 μm, length=50 cm) was 2.31 second. After finishing the reaction, an aliquot of the product solution was taken (15 sec) and was analyzed by GC (column, CBP1; 0.25 mm×25 m; initial oven temperature, 50° C.; rate of temperature increase, 10° C./min). As a result, 2-bromophenyldimethylsilane (GC retention time: 14.9 min) was obtained in 68% yield. $^1$H NMR (400 MHz, CDCl$_3$) δ: 0.40-0.43 (m, 6H), 4.47-4.53 (m, 1H), 7.14-7.27 (m, 2H), 7.42-7.50 (m, 2H); $^{13}$C NMR (100 MHz, CDCl$_3$) δ: −3.5, 126.4, 130.6, 130.9, 132.2, 136.4, 139.1. HRMS (EI) m/z: calcd. for C$_8$H$_{11}$BrSi 213.9813, found 213.9816.

Example 10

E$_1$=SiMe$_3$ and X$_2$=Br in Formula (IV)

The present invention was carried out using the same microreactor apparatus, as shown in FIG. 3, except that the inner diameter and the length of the second tube reactor and the residence time thereof were changed.

A microsystem composed of three T-shaped micromixers (M1, M2 and M3) and two microtube reactors (R1 and R2) was used. The whole microsystem was dipped in a cooling bath (−78° C.). A solution of o-dibromobenzene (0.27 M) in THF (flow rate: 6 mL/min, 1.62 mmol/min) and a solution of n-BuLi (1.5 M) in n-hexane (flow rate: 1.2 mL/min, 1.8 mmol/min) were introduced to the first T-shaped mixer M1 (inner diameter: 250 μm) by using syringe pumps. The resulting solution was passed through the tube reactor R1 and was mixed with trimethylsilyl trifluoromethanesulfonate (Me$_3$SiOTf) (0.65 M) in Et$_2$O (flow rate: 3 mL/min, 1.95 mmol/min) in the second T-shaped mixer M2 (inner diameter: 500 μm). The resulting solution was passed through the tube reactor R2 and was introduced to the third T-shaped mixer M3 (inner diameter: 500 μm), where the solution was quenched with methanol (neat, flow rate=3.0 mmol/min). The residence time of the tube reactor R1 (inner diameter: 500 μm, length=50 cm) was 0.82 second. The residence time of the tube reactor R2 (inner diameter: 1,000 μm, length=100 cm) was 4.62 second. After finishing the reaction, an aliquot of the product solution was taken (15 sec) and was analyzed by GC (column, CBP1; 0.25 mm×25 m; initial oven temperature, 50° C.; rate of temperature increase, 10° C./min). As a result, 2-bromophenyltrimethylsilane (GC retention time: 15.9 min) was obtained in 69% yield. $^1$H NMR (400 MHz, CDCl$_3$) δ: 0.39 (s, 9H), 7.18 (dt, J=8.0, 2.0 Hz, 1H), 7.26 (dt, J=8.0, 2.0 Hz, 1H), 7.42 (dd, J=7.6, 1.6 Hz, 1H), 7.51 (dd, J=7.6, 1.6 Hz, 1H) $^{13}$C NMR (100 MHz, CDCl$_3$) δ: −0.4, 126.2, 130.4, 130.5, 132.6, 135.9, 141.0. HRMS (EI) m/z: calcd. for C$_9$H$_{13}$BrSi 227.9970, found 227.9967.

Example 11

E$_1$=SnBu$_3$ and X$_2$=Br in Formula (IV)

The present invention was carried out using the same microreactor apparatus, as shown in FIG. 3, except that the residence time of the second tube reactor was changed.

A microsystem composed of three T-shaped micromixers (M1, M2 and M3) and two microtube reactors (R1 and R2) was used. The whole microsystem was dipped in a cooling bath (−78° C.). A solution of o-dibromobenzene (0.27 M) in THF (flow rate: 6 mL/min, 1.62 mmol/min) and a solution of n-BuLi (1.5 M) in n-hexane (flow rate: 1.2 mL/min, 1.8 mmol/min) were introduced to the first T-shaped mixer M1 (inner diameter: 250 μm) by using syringe pumps. The resulting solution was passed through the tube reactor R1 and was mixed with chlorotributylstannane (Bu$_3$SnCl) (0.32 M) in THF (flow rate: 6 mL/min, 1.92 mmol/min) in the second T-shaped mixer M2 (inner diameter: 500 μm). The resulting solution was passed through the tube reactor R2 and was introduced to the third T-shaped mixer M3 (inner diameter: 500 μm), where the solution was quenched with methanol (neat, flow rate=3.0 mmol/min). The residence time of the tube reactor R1 (inner diameter: 500 μm, length=50 cm) was 0.82 second. The residence time of the tube reactor R2 (inner diameter: 1,000 μm, length=50 cm) was 1.78 second. After finishing the reaction, an aliquot of the product solution was taken (15 sec) and was concentrated, then the residue was subjected to silica gel column chromatography (hexane) to refine, 2-bromophenyltributylstannane was obtained as colorless oil in 81% yield, 146.6 mg. $^1$H NMR (400 MHz, CDCl$_3$) δ: 0.88 (t, J=7.2 Hz, 9H), 1.12-1.17 (m, 6H), 1.27-1.38 (m, 6H), 1.51-1.60 (m, 6H), 7.10-7.15 (dt, J=7.6, 1.6 Hz, 1H), 7.18-7.23 (dt, J=7.6, 1.2 Hz, 1H), 7.27-7.31 (dd, J=7.6, 1.6 Hz, 1H), 7.44-7.50 (dd, J=7.6, 1.6 Hz, 1H); $^{13}$C NMR (100 MHz, CDCl$_3$) δ: 11.0, 13.8, 27.4, 29.1, 126.1, 129.8, 131.5, 133.2, 137.8, 146.5. HRMS (EI) m/z: calcd. for C$_{14}$H$_{22}$BrSn (M$^+$−C$_4$H$_9$) 388.9927, found 388.9925.

Example 12

E$_1$=CH(OH)Ph and X$_2$=Br in Formula (IV)

The present invention was carried out using the same microreactor apparatus, as shown in FIG. 3, except that the length of the second tube reactor and the residence time thereof were changed.

A microsystem composed of three T-shaped micromixers (M1, M2 and M3) and two microtube reactors (R1 and R2) was used. The whole microsystem was dipped in a cooling bath (−78° C.). A solution of o-dibromobenzene (0.27 M) in THF (flow rate: 6 mL/min, 1.62 mmol/min) and a solution of n-BuLi (1.5 M) in n-hexane (flow rate: 1.2 mL/min, 1.8 mmol/min) were introduced to the first T-shaped mixer M1 (inner diameter: 250 μm) by using syringe pumps. The resulting solution was passed through the tube reactor R1 and was mixed with benzaldehyde (0.65 M) in THF (flow rate: 3 mL/min, 1.95 mmol/min) in the second T-shaped mixer M2 (inner diameter: 500 μm). The solution was introduced to the third T-shaped mixer M3 (inner diameter: 500 μm), where the solution was quenched with methanol (neat, flow rate=3.0 mmol/min). The residence time of the tube reactor R1 (inner diameter: 500 μm, length=50 cm) was 0.82 second. The residence time of the tube reactor R2 (inner diameter: 1,000 μm, length=150 cm) was 6.93 second. After finishing the reaction, an aliquot of the product solution was taken (15 sec) and was analyzed by GC (column, CBP1; 0.25 mm×25 m; initial oven temperature, 50° C.; rate of temperature increase, 10° C./min). As a result, (2-bromophenyl)phenylmethanol (GC retention time: 23.7 min) was obtained in 75% yield. $^1$H NMR (400 MHz, CDCl$_3$) δ: 2.59-2.78 (m, 1H), 6.11 (s, 1H), 7.09 (dt, J=7.6, 2.0 Hz, 1H), 7.19-7.36 (m, 6H), 7.47-7.54 (m, 2H);

$^{13}$C NMR (100 MHz, CDCl$_3$) δ: 74.7, 122.6, 126.9, 127.51, 127.53, 128.25, 128.29, 128.9, 132.6, 141.9, 142.3.

Example 13

E$_1$=CH(OH)Ph and X$_2$=Br in Formula (IV)

The present invention was carried out using the same microreactor apparatus, as shown in FIG. 3, except that the length of the second tube reactor and the residence time thereof were changed.

A microsystem composed of three T-shaped micromixers (M1, M2 and M3) and two microtube reactors (R1 and R2) was used. The whole microsystem was dipped in a cooling bath (−78° C.). A solution of o-dibromobenzene (0.27 M) in THF (flow rate: 6 mL/min, 1.62 mmol/min) and a solution of n-BuLi (1.5 M) in n-hexane (flow rate: 1.2 mL/min, 1.8 mmol/min) were introduced to the first T-shaped mixer M1 (inner diameter: 250 μm) by using syringe pumps. The resulting solution was passed through the tube reactor R1 and was mixed with acetophenone (0.65 M) in THF (flow rate: 3 mL/min, 1.95 mmol/min) in the second T-shaped mixer M2 (inner diameter: 500 μm). The solution was introduced to the third T-shaped mixer M3 (inner diameter: 500 μm), where the solution was quenched with methanol (neat, flow rate=3.0 mmol/min). The residence time of the tube reactor R1 (inner diameter: 500 μm, length=50 cm) was 0.82 second. The residence time of the tube reactor R2 (inner diameter: 1,000 μm, length=75 cm) was 3.46 second. After finishing the reaction, an aliquot of the product solution was taken (15 sec) and was analyzed by GC (column, CBP1; 0.25 mm×25 m; initial oven temperature, 50° C.; rate of temperature increase, 10° C./min). As a result, 1-(2-bromophenyl)-1-phenylethanol (GC retention time: 23.5 min) was obtained in 81% yield. $^1$H NMR (400 MHz, CDCl$_3$) δ: 1.95 (s, 3H), 3.49 (s, 1H), 7.16 (dt, J=7.6, 1.6 Hz, 1H), 7.20-7.30 (m, 5H), 7.38 (dt, J=7.6, 1.2 Hz, 1H), 7.52 (dd, J=8.0, 1.2 Hz, 1H), 7.80 (dd, J=7.6, 2.0 Hz, 1H); $^{13}$C NMR (100 MHz, CDCl$_3$) δ: 30.4, 77.4, 122.2, 125.4, 126.7, 127.2, 128.0, 128.3, 129.0, 134.7, 144.7, 147.4. HRMS (EI) m/z: calcd. for C$_{14}$H$_{13}$BrO 276.0150, found 276.0155.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority on Patent Application No. 2007-031346 filed in Japan on Feb. 9, 2007, each of which is entirely herein incorporated by reference.

What we claim is:

1. A method of producing an o-disubstituted aromatic compound, comprising: continuously conducting at least the following steps:
   (a) a step of mono-lithiating one halogen atom of an o-dihaloaromatic compound, using a first microreactor;
   (b) a step of making the thus-obtained monolithiated product to react with an electrophilic compound, using a second microreactor, to obtain a monosubstituted-monohaloaromatic compound;
   (c) a step of lithiating the other halogen atom of the o-dihaloaromatic compound, using a third microreactor; and
   (d) a step of making the thus-obtained lithiated product successively to react with an electrophilic compound, using a fourth microreactor, wherein a reaction temperature in a flow channel of each of the first microreactor and the second microreactor is in the range of from −85° C. to −60° C.

2. The method of producing an o-disubstituted aromatic compound as claimed in claim 1, wherein the electrophilic compound to be used is an aldehyde compound, a ketone compound, a chlorosilane compound, a chlorostannane compound, a halogenated alkyl compound, a sulfonic acid ester compound, or a boric acid ester compound.

3. The method of producing an o-disubstituted aromatic compound as claimed in claim 1, wherein the minimum length of a flow channel cross-section of the first microreactor is in the range of from 10 μm to 800 μm, and the minimum length of a flow channel cross-section of each of the second to fourth microreactors is independently in the range of from 10 μm to 5,000 μm.

4. A method of selectively producing a monosubstituted-monohaloaromatic compound, comprising: continuously conducting at least the following steps:
   (a) a step of mono-lithiating one halogen atom of an o-dihaloaromatic compound, using a first microreactor; and
   (b) a step of making the thus-obtained monolithiated product to react with an electrophilic compound, using a second microreactor, to obtain a monosubstituted-monohaloaromatic compound, wherein a reaction temperature in a flow channel of each of the first microreactor and the second microreactor is in the range of from −85° C. to −60° C.

5. The method of selectively producing a monosubstituted-monohaloaromatic compound as claimed in claim 4, wherein the electrophilic compound to be used is an aldehyde compound, a ketone compound, a chlorosilane compound, a chlorostannane compound, a halogenated alkyl compound, a sulfonic acid ester compound, or a boric acid ester compound.

6. The method of selectively producing a monosubstituted-monohaloaromatic compound as claimed in claim 4, wherein the minimum length of a flow channel cross-section of the first microreactor is in the range of from 10 μm to 800 μm, and the minimum length of a flow channel cross-section of the second microreactor is in the range of from 10 μm to 5,000 μm.

* * * * *